(12) United States Patent
Soll et al.

(10) Patent No.: US 7,262,214 B2
(45) Date of Patent: Aug. 28, 2007

(54) 1-N-ARYLPYRAZOLE DERIVATIVES IN PREVENTION OF ARTHROPOD-BORNE AND MOSQUITO-BORNE DISEASES

(75) Inventors: Mark Soll, Alpharetta, GA (US);
Albert Boeckh, Cumming, GA (US)

(73) Assignee: Merial Limited, Duluth, GA (US)

( * ) Notice: Subject to any disclaimer, the term of this patent is extended or adjusted under 35 U.S.C. 154(b) by 199 days.

(21) Appl. No.: 10/374,627

(22) Filed: Feb. 26, 2003

(65) Prior Publication Data
US 2004/0167175 A1 Aug. 26, 2004

(51) Int. Cl.
*A01N 43/56* (2006.01)
(52) U.S. Cl. ............. 514/407; 424/405; 424/406; 424/407; 424/409; 424/84
(58) Field of Classification Search ......... 424/405, 424/406; 514/407, 30
See application file for complete search history.

(56) References Cited

U.S. PATENT DOCUMENTS 5,567,429 A * 10/1996 Senbo ............... 424/405
6,096,329 A * 8/2000 Jeannin ............. 424/405
6,482,425 B1 * 11/2002 Huet et al. ......... 424/406

OTHER PUBLICATIONS

The yearbook of agriculture—Animal Diseases ; pp. 75-79,177-180,550-555; 1956.*
The Merck Veterinary Manual ; pp. 731-734; 1967.*
Washington Post-Express Birds Decimated by West Nile Virus, May 17, 2007, p. 3.*

* cited by examiner

*Primary Examiner*—Neil S. Levy
(74) *Attorney, Agent, or Firm*—Thomas J. Kowalski; Judy Jarecki-Black; Frommer Lawrence & Haug

(57) ABSTRACT

This invention provides for a method for preventing or interrupting the transmission of anthropod and mosquito-borne diseases from a first actual or putative amplifying or incipient host to a second actual or putative amplifying or incipient host, which comprises applying or administering a formulation comprising an effective amount of at least one 1-N-arylpyrazole to said first actual or putative amplifying host and/or actual or putative amplifying or incipient host. This invention also provides for a method of using a bait placed in a bird station, the bait comprises an affective amount of at least one 1-N-arylpyrazole either alone or in combination with an antiparasitic, antihelmintic, or insecticidal agents. This invention also provides for an apparatus for delivering an effective amount of a formulation according to the present invention to a bird or animal in an environment where it resides.

28 Claims, 2 Drawing Sheets

1-N-ARYLPYRAZOLE DERIVATIVES IN PREVENTION OF ARTHROPOD-BORNE AND MOSQUITO-BORNE DISEASES

FIELD OF THE INVENTION

This invention relates to spot-on formulations for preventing or interrupting the transmission of arthropod- and mosquito-borne diseases from an animal, bird or human, which may or may not be infected with the disease, to a second animal, bird or human. In particular, this invention provides for a method of preventing or interrupting the transmission of a mosquito-borne disease in an animal, bird or human to a second animal, bird or human by administering a formulation comprising an 1-N-arylpyrazole derivative. This invention also provides the use of a bait comprising at least one 1-N-arylpyrazole derivative and/or an IGR either alone or in combination with any antiparasitic, antihelmintic, or insecticidal agent placed in a commercially available bird station for preventing or interrupting the transmission of arthropod- and mosquito-borne diseases from an actual or putative amplifying or incipient host, such as an animal or bird (wild or domesticated), to a second actual or putative amplifying or incipient host, such as an animal, bird or human.

This invention further provides an apparatus to administer a spot-on or pour-on formulation according to the present invention to animals, both domesticated and wild.

All of the applications, as well as all documents cited herein and documents referenced or cited in documents cited herein, are hereby incorporated herein by reference.

BACKGROUND OF THE INVENTION

Mosquitoes act as vectors for a number of viral and protozoal infections in the world. It has been reported that mosquitoes carry diseases that potentially compromise the health of one-eighth of the world's population and impact the health and economy of approximately 300 million people per year.

In addition to clinically significant diseases like malaria and yellow fever, mosquitoes are also implicated in the transmission of many arboviruses, infections with which cause symptoms ranging from nonspecific flu-like illnesses to encephalitis that may result in death. In addition to humans, domesticated animals such as dogs, cats, horses, cattle, sheep, pigs, as well as wild animals and birds may become infected and experience clinical disease as a result of that infection.

Arboviruses that infect humans and other mammals are members of one of three virus families, Togaviridae, Flavividae, and Bunyaviridae, and include the agent responsible for Eastern Equine Encephalitis (EEE), Western Equine Encephalitis (WEE), St. Louis Encephalitis (SLE), La Crosse Encephalitis (LCE), and infection caused by Dengue Virus, and West Nile Virus (WNV). Worldwide, other arboviruses of medical importance include viruses responsible for Japanese Encephalitis (JE) and Venezuelan Equine Encephalitis.

WNV has received significant attention in the United States since its outbreak on the East Coast in 1999 and 2000. Since that outbreak, CDC estimates that WNV has been documented in forty-three of the lower forty-eight states including areas as geographically diverse as Alabama, Arkansas, California, Colorado, and North Dakota. From 1999 through 2001, there were 149 cases of WNV human illness reported to the CDC, including 18 deaths (see www.cdc.gov/ncidod/dvbid/westnile/background.htm).

Transmission of WNV is similar to EEE, WEE, SLE viruses and may involve a cycle that includes mosquitoes and birds. Mosquitoes become infected with WNV when they feed on a bird carrying the virus in its blood. Birds act as amplifying hosts for the virus and, ten to fourteen days after initial infection, the virus can be transmitted to another bird, a human, or another animal host when the mosquito injects saliva containing the virus into that host during feeding. At present, the CDC reports that there are 110 species of birds that may act as amplifying hosts for WNV. Additionally, infected birds may facilitate the spread of the disease as birds can fly long distances after becoming infected.

While humans and other animals may become clinically ill after infection with WNV, they are considered to be incidental hosts since they do not develop enough of the virus in the blood to infect other hosts. Arboviruses other than WNV have different amplifying hosts. For example, the amplifying hosts for JE virus are domestic pigs and wild birds (www.cdc.gov/nicidod/dvbid/jecephalitis/qa.htm), while the amplifying hosts for the virus that causes La Crosse encephalitis are chipmunks and tree squirrels (www.cdc.gov/nicod/dsbid/arbor/ardet.htm).

Another emerging mosquito-borne disease of veterinary importance is heartworm disease, caused by infection with *Dirofilaria immitis*, and characterized by several developmental stages. Specifically, microfilariae are deposited by female heartworms into the bloodstream of a definitive host—primarily canines, but also felines and ferrets. Once ingested by a mosquito during feeding, the microfilariae develop into infective larvae which, when transmitted to the definitive host, migrate to heart where maturation into adult worms occurs. A number of drug treatments have been developed to treat heartworm. For example, U.S. Pat. No. 5,550,153 to Kerz discloses the use of Ivermectin for treating *Dirofilaria immitis* infection in canines.

Other research has been directed to the control of heartworm and other arthropod-borne diseases by interfering with transmission cycles. For example, the most common method for controlling mosquitoes that transmit harmful viruses or other microorganisms involves spraying insecticides into areas where the mosquitoes breed. This approach is not without risk, however. For example, the use of insecticides may have a harmful environmental impact, especially to the wetland areas where mosquitos often reside (see, e.g., US 2002/021045 A1). Thus, there is a need for simple, low cost methods to abate arthropod populations, including mosquitos and ticks, and to prevent or impair the transmission of mosquito-borne diseases without widespread environmental damage.

1-N-arylpyrazoles as a class of chemicals are well known in the art, as are methods for their use in controlling parasites including insects, such as fleas or ticks, in mammals, such as domesticated livestock or companion animals, either alone or in combination with other pesticides such as insect growth regulators. See, e.g., EP-A-295,217, EP 295 177, EP-A-840-686, EP-A-352,944, WO 00/35844, WO 98/39972, U.S. Pat. Nos. 5,122,530 5,236,938, 5,232,940, 5,576,429 5,814,652, 5,567,429, 6,090,751 and 6,096,329 as well as Publication No. US 2002-90381-A1. See also copending applications U.S. Ser. Nos. 07/719,942; 08/933, 016; 09/174,598; 08/863,182; and 08/863,692. The compounds of the families defined in these patents are extremely active and one of these compounds, 5-amino-3-cyano-1-(2, 6-dichloro-4-trifluoromethylphenyl)-4-trifluoromethylsulfinylpyrazole, or fipronil, is particularly effective, but not exclusively effective, against fleas and ticks. However, specific results involving the effectiveness of these compounds against mosquitoes generally have not been reported.

Various methods of formulating antiparasitical formulations are known in the art. These include oral formulations, baits, dietary supplements, powders, shampoos, etc. Formulations for localized topical applications of antiparasitical formulations are also known in the art. For example, pour-on solutions comprising 1-N-phenylpyrazole derivatives, such as fipronil, are known in the art and are described in copending application Ser. No. 08/933,016, now U.S. Pat. Nos. 6,010,710, and 6,413,542, issued Jul. 2, 2002 and copending application Ser. No. 10/120,691, filed Apr. 11, 2002 and herein incorporated by reference. Other methods of formulating antiparasitic agents include spot-on formulations.

Spot-on formulations are well known techniques for topically delivering an antiparasitic agent to a limited area of the host. For example, U.S. Pat. No. 5,045,536 describes such formulations for ectoparasites. Other spot-on formulations include U.S. Pat. No. 6,426,333 and copending application U.S. Ser. No. 09/221,470, now allowed, and 10/155,397, filed on May 24, 2002. WO 01/95715 describes a method for controlling ectoparasites in small rodents as well as interrupting or preventing the diseases caused by arthropods of small rodents, which comprise applying topical formulations, such as spot-on compositions, to the skin, or hair of the rodents. WO 01/95715 further provides an enclosure having one or more peripheral openings, which allows the entry and egress of rodents, and an applicator, which comprises the topical formulation and is arranged to contact a rodent. However, WO 01/95715 does not describe a method for preventing or interrupting the transmission of mosquito-borne diseases, in general, or the transmission of WNV, in particular, by administering a formulation comprising a 1-N-phenylpyrazole to a host, in general, or birds, in particular, thereby affecting a simple, low-cost method to abate mosquito populations and to prevent or impair the transmission of mosquito-borne diseases without widespread environmental damage.

Baits are another method of formulating that is known in the art. For example, U.S. patent application Ser. No. 4,564,631 to Elbert et al. relates to a process of preparing a bait containing Pyrethroids for combating Vermin. However, no methods are known to use a commercially available bird station (for example, see bird stations sold by Wild Bird Station, 2295 NW Broad street Murfreesboro, Tenn. 37129 or visit info@wildbirdstation.com) having baits comprising 1-N-arylpyrazole derivatives and/or an IGR either alone or in combination with a known antiparasitic, antihelmintic or insecticidal agent to prevent or to interrupt the transmission of arthropod- or mosquito-borne diseases by birds or other small mammalian hosts.

SUMMARY OF THE INVENTION

The present invention provides for, inter alia, a method for preventing or interrupting the transmission of arthropod- or mosquito-borne diseases from a putative amplifying host, such as an animal, bird or human, to a second putative amplifying or incipient host, such as an animal, bird or human, which comprises applying or administering a formulation comprising an effective amount of at least one 1-N-arylpyrazole derivative to said first actual or putative amplifying or incipient host and/or second actual or putative amplifying or incipient host.

This invention further provides for a method for preventing or interrupting the transmission of mosquito-borne diseases from an actual or putative amplifying or incipient host, such as an animal or bird (wild or domesticated), to a second actual or putative amplifying or incipient host, such as an animal, bird or human, by applying a spot-on formulation comprising:
  (a) an effective amount of at least one 1-N-arylpyrazole derivative;
  (b) a pharmaceutically or veterinary acceptable liquid carrier vehicle;
  (c) optionally, an insect growth regulator and/or a crystallization inhibitor to said first actual or putative amplifying host and/or to said second actual or putative amplifying or incipient hosts.

This invention further provides for a method for preventing or interrupting the transmission from an actual or putative amplifying incipient host, such as a bird, animal or human, to a second actual or putative amplifying or incipient host, such as a bird, animal or human, by applying a pour-on formulation comprising:
  (a) an effective amount of at least one 1-N-arylpyrazole derivative;
  (b) a pharmaceutically or veterinary acceptable liquid carrier vehicle;
  (c) optionally, an insect growth regulator and/or a crystallization inhibitor to said first actual or putative amplifying or incipient host and/or second actual or putative amplifying or incipient host.

This invention also provides the use of a commercially available bird station having a bait comprising an effective amount of at least one 1-N-arylpyrazole derivative and/or an IGR either alone or in combination with any known antiparasitic, antihelmintic, or insecticidal agent(s) including but not limited to Pyrethroids, Avermectins, Organophosphates, Carbamates, Neonicotinoids or a mixture thereof.

Also provided within scope of the present invention is an apparatus, as well as a method of using this apparatus, to administer the spot-on or pour-on formulations according to the present invention to birds or animals, both domesticated and wild, thereby preventing or interrupting the transmission of the mosquito-borne disease from said birds or animals to a second actual or putative amplifying or incipient host, which may be another bird or animal or a human.

BRIEF DESCRIPTION OF THE DRAWINGS

A full and enabling disclosure of the present invention, including the best mode thereof, to one of ordinary skill in the art, is set forth more particularly in the remainder of the specification, including reference to the accompanying figures, wherein.

DETAILED DESCRIPTION

Figure 1:
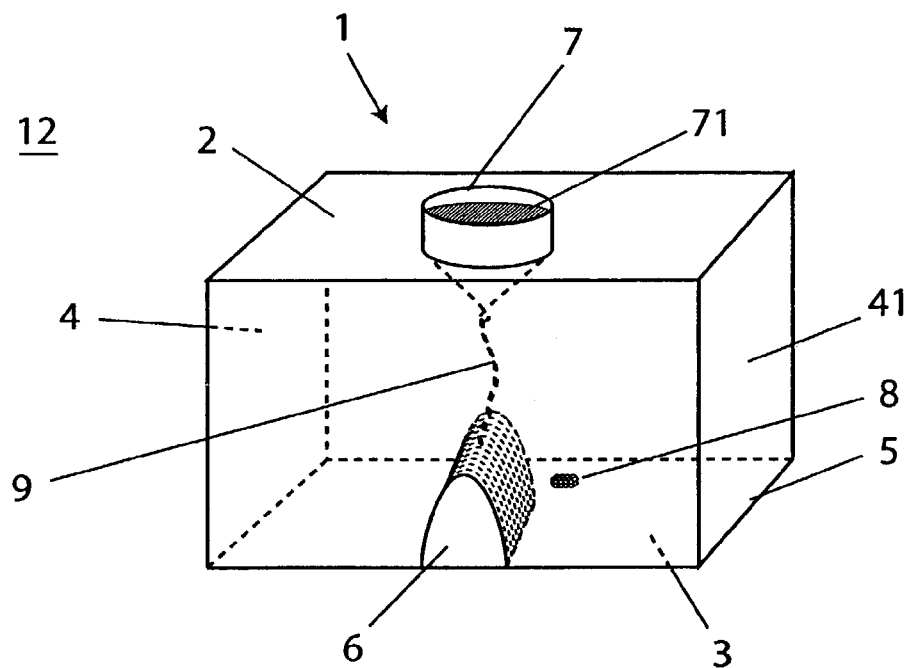
FIG. 1 depicts one embodiment of an apparatus of the present invention for delivering a dose of a veterinary formulation to a bird or mammal.
Figure 2:
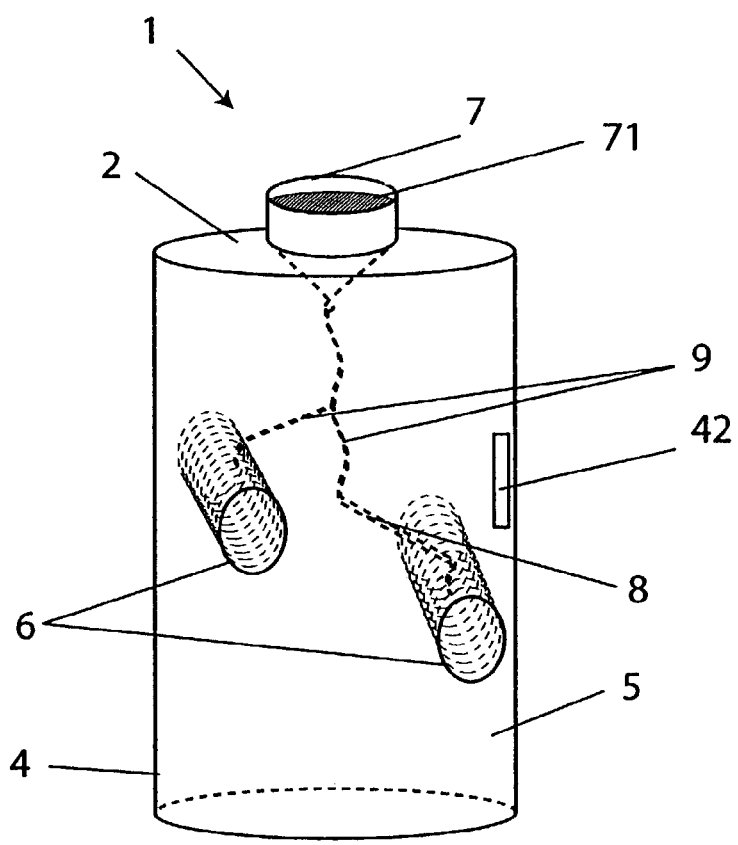
FIG. 2 depicts another embodiment of the inventive apparatus.

Other objects, features and aspects of the present invention are disclosed in, or are obvious from, the following Detailed Description. It is to be understood by one of ordinary skill in the art that the present discussion is a description of exemplary embodiments only and is not intended as limiting the broader aspects of the present invention, which broader aspects are embodied in the exemplary construction. In fact, it will be apparent to those skilled in the art that various modifications and variations can be made in the present invention without departing from the scope or spirit of the invention. For instance, features illustrated or described as part of one embodiment can be used in another embodiment to yield a still further embodiment. It is intended that the present invention cover such modifications and variations as come within the scope of the appended claims and their equivalents.

For convenience, certain terms employed in the Specification, Examples, and appended Claims are collected here.

Definitions: As used herein, the term "comprising" in this disclosure can mean "including" or can have the meaning commonly given to the term "comprising" in U.S. Patent Law.

Parasitic diseases may be caused by either endoparasites or ectoparasites. As used herein endoparasites refer to those parasites living inside the body of the host, either within an organ (such as the stomach, lungs, heart, intestines, etc.) or simply under the skin. Ectoparasites are those parasites that live on the outer surface of the host but still draw nutrients from the host. Endoparasitic diseases may further be subdivided based on class of parasite involved in the infection. For example, endoparasitic diseases generally referred to as helminthiasis are due to infection of the host with parasitic worms known as helminths. Helminthiasis is a prevalent and serious worldwide economic problem due to infection of domesticated animals such as swine, sheep, horses, cattle, goats, dogs, cats, and poultry. Many of these infections, caused by the group of worms described as nematodes, cause diseases in various species of animals throughout the world. These diseases are frequently serious and can result in the death of the infected animal. The most common genera of nematodes infecting the animals referred to above include, but are not limited to, Haemonchus, Trichostrongylus, Ostertagia, Nematodirus, Cooperia, Ascaris, Bunostomum, Oesophagostomum, Chabertia, Trichuris, Strongylus, Trichonema, Dictyocaulus, Capillaria, Heterakis, Toxocara, Ascaridia, Oxyuris, Ancylostoma, Uncinaria, Toxascaris, and Parascaris. Many parasites are species specific (infect only one host) and most also have a preferred site of infection within the animal. Thus, Haemonchus and Ostertagia primarily infect the stomach while Nematodirus and Cooperia mostly attack the intestines. Other endoparasites reside in the heart, eyes, lungs, blood vessels, and the like while still others are subcutaneous parasites. Helminthiasis can lead to weakness, weight loss, anemia, intestinal damage, malnutrition, and damage to other organs. If left untreated these diseases can result in the death of the animal.

Examples of endoparasites which infect animal and man include but are not limited to gastrointestinal parasites of the genera *Ancylostoma, Necator, Ascaris, Strongyloides, Trichinella, Capillaria, Trichuris, Enterobius*, and the like. Other endoparasites which infect animal and man are found in the blood or in other organs. Examples of such parasites include but are not limited to filarial worms Wuchereria, *Brugia, Onchocerca*, and the like as well as extra-intestinal stages of the intestinal worms *Strongylides* and *Trichinella*. Ectoparasites which parasitize man include arthropods such as ticks, fleas, mites, lice, and the like and, as with domestic animals, infections by these parasites can result in transmission of serious and even fatal diseases.

Infestations by ectoparasitic arthropods including but not limited to ticks, mites, lice, stable flies, hornflies, blowflies, fleas, and the like are also a serious problem. Infection by these parasites results not only in loss of blood and skin lesions, but also can interfere with normal eating habits thus causing weight loss. Ectoparasitic infestations of a host can also result in transmission of serious diseases including but not limited to encephalitis, anaplasmosis, babesiosis, rocky mountain spotted fever, lyme disease, ehrlichiosis, swine pox, and the like, many of which can be fatal to the host. Animals may be infected by several species of parasite at the same time since infection by one parasite may weaken the animal and make it more susceptible to infection by a second species of parasite.

The compounds of this invention are also active against household pests including but not limited to cockroach, *Blatella* sp., clothes moth, *Tineola* sp., carpet beetle, *Attagenus* sp. and the housefly *Musca domestica* and against *Solenopsis invicta* (imported fire ants), termites, and the like.

These compounds are furthermore useful against agricultural pests such as aphids (*Acyrthiosiphon* sp.) locusts, and boll weevils as well as against insect pest which attack stored grains such as *Tribolium* sp. and against immature stages of insects living on plant tissue. The compounds are also useful as anematodicide for the control of soil nematodes which may be agriculturally important.

Antiparasitic agents are also useful for the treatment and/or prevention of helminthiasis in domestic animals such as cattle, sheep, horses, dogs, cats, goats, swine, and poultry. They are also useful in the prevention and treatment of parasitic infections of these animals by ectoparasites such as ticks, mites, lice, fleas and the like. They are also effective in the treatment of parasitic infections of humans.

Antiparasitic agents as used herein including ecto- and endo-parsidicale agents include but are not limited to: albendazole, amitraz, amprolium, antimony, atovaquaone, benzimidazole, bunamidine, dichlorvos, diethylcarbamazine, diminazene aceturate, disophenol, dithiazanine iodide, epsiprantal, fenbendazole, fenthion, furazolidine, imidocarb dipropionate, ipronidazole, ivermectin, levamisole, lime sulfur suspension, lufenuron, mebendazole, meglumine antimonite, melarsomine HCl, metronidazole, milbemycin oxime, moxidectin, naproxen, niclosamide, nilurtimox, paromomycin, parvaquone, pentamidine isethionate, phenamidine isethionate, piperazine, praziquantel, primaquine phosphate, primaquine PO4, pyrantel pamoate, pyrimethamine, quinacrine, selamectin, skin so soft by avon, sodium stibogluconate, spiramycin, styrylpyridinium DEC, sulfadiazine, trimethoprim, sulfadimethoxine, sulfamethazine, tetramisole, thiabendazole, toltrazuril, toluene, trimetraxate glucuronate, trypan blue, and the like.

Antihelmintics agents as used herein include, but are not limited to benzoimidazoles such as thiobendazole, mebendazole, albendazole and the like.

Insecticidal agents as used herein include but are not limited to organophosphates such as coumaphos, carbamates such as propoxur, pyrethroids such as permethrin, arylpyrazoles such as fipronil, neonicotinoids such as imidaclopid and avermectins such as ivermectin and the like.

As discussed above, the 1-N-arylpyrazole derivatives contemplated in the present invention as methods to formulate these compounds are known in the art. This class of insecticides is known to possess excellent activity against insects, such as ticks and fleas.

The formulations contemplated in the method for preventing or interrupting the transmission of arthropod- and mosquito-borne diseases from an actual or putative amplifying host, such as an animal (domestic or wild), bird (domestic or wild) or human, to a second actual putative amplifying or incipient host comprise a therapeutically effective amount of at least 1-N-phenylpyrazole and optionally at least one diluent or carrier: the diluent or carrier would be well know to a practitioner of this art. Carriers include organic or inorganic materials, natural or synthetic, that facilitate the administration of the 1-N-arylpyrazole derivatives to the animal, bird or human. Non-limiting examples of carriers include clays, silicates, silica, resins or waxes. Non-limiting examples of diluents include water, alcohols, ketones, oil solvent, polyethylene glycol and polar aprotic solvents such as corn oil, or dimethylsulfoxide. Preferred 1-N-arylpyrazole derivatives include those described below for the spot-on and pour-on formulations. Routes of administration include oral, parenteral, e.g., subcutaneous or intravenous, or topical, such as sprays.

Preferred formulations for the inventive method comprise:

A) an effective amount of at least one compound of the formula:

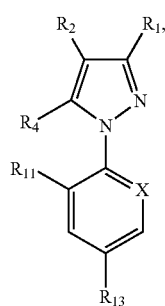

(I)

in which:
$R_1$ is a halogen atom, CN or alkyl;
$R_2$ is $S(O)_n R_3$ or 4,5-dicyanoimidazol-2-yl or haloalkyl;
$R_3$ is alkyl, alkenyl, alkynyl, haloalkyl, haloalkenyl or haloalkyl;
$R_4$ is hydrogen, halogen, $NR_5R_6$, $S(O)_m R_7$, $C(O)R_7$, $C(O)OR_7$, alkyl, haloalkyl, $OR_8$ or $-N=C(R_9)(R_{10})$ substituent;
$R_5$ and $R_6$ independently represent a hydrogen atom, alkyl, haloalkyl, C(O)alkyl, $S(O)_r CF_3$ or alkoxycarbonyl or $R_5$ and $R_6$ together may combine to form a ring of 5 to 7 members.
$R_7$ represents an alkyl or haloalkyl group;
$R_8$ represents an alkyl, haloalkyl or a hydrogen;
$R_9$ represents an alkyl or a hydrogen;
$R_{10}$ represents an optionally substituted aryl or an optionally substituted heteroaryl group;
$R_{11}$ and $R_{12}$ represent, independently of one another, hydrogen, halogen CN or $NO_2$;
$R_{13}$ represents a halogen atom or a haloalkyl, haloalkoxy, $S(O)_q CF_3$ or $SF_5$ group;
m, n, q and r represent, independently of one another, an integer equal to 0, 1 or 2;
X represents a trivalent nitrogen atom or a C—$R_{12}$, the three other valencies of the carbon atom forming part of the aromatic ring;
optionally with a pharmaceutically acceptable carrier or excipient.

Preferred spot-on compositions to be used in the inventive method include, for example, spot-on formulations comprising:

(a) an effective amount of at least one compound of the formula

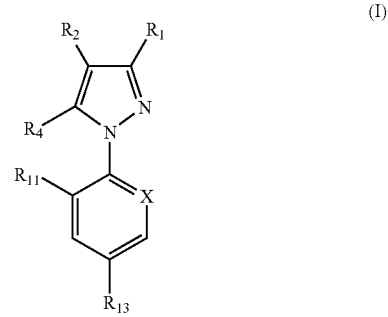

(I)

in which:
$R_1$ is a halogen atom, CN or methyl;
$R_2$ is $S(O)_n R_3$ or 4,5-dicyanoimidazol-2-yl or haloalkyl;
$R_3$ is alkyl, haloalkyl, haloalkenyl or haloalkynyl;
$R_4$ represents a hydrogen or halogen atom or an $NR_5R_6$, $S(O)_m R_7$, $C(O)R_7$ or $C(O)OR_7$, alkyl, haloalkyl or $OR_8$ or an $-N=C(R_9)(R_{10})$ group;
$R_5$ and $R_6$ independently represent a hydrogen atom or an alkyl, haloalkyl, C(O)alkyl, $S(O)_r CF_3$ or alkoxycarbonyl group or $R_5$ and $R_6$ together may form a ring of 5 to 7 members;
$R_7$ represents an alkyl or haloalkyl substituent;
$R_8$ represents an alkyl or haloalkyl or a hydrogen;
$R_9$ represents an alkyl or a hydrogen atom;
$R_{10}$ represents an optionally substituted aryl or an optionally substituted heteroaryl group;
$R_{11}$ and $R_{12}$ represent, independently of one another, hydrogen, halogen CN or $NO_2$;
$R_{13}$ represents a halogen atom or a haloalkyl, haloalkoxy, $S(O)_q CF_3$ or $SF_5$ group;
m, n, q and r represent, independently of one another, an integer equal to 0, 1 or 2;
X represents a trivalent nitrogen atom or a C—$R_{12}$, the three other valencies of the carbon atom forming part of the aromatic ring;

with the proviso that, when $R_1$ is methyl, then either $R_3$ is haloalkyl, $R_4$ is $NH_2$,
$R_{11}$ is Cl, $R_{13}$ is $CF_3$ and X is N or else $R_2$ is 4,5-dicyanoimidazol-2-yl, $R_4$ is Cl, $R_{11}$ is Cl, $R_{13}$ is $CF_3$ and X is C—Cl; and/or (b) a pharmaceutically or veterinary acceptable liquid carrier vehicle; and (c) optionally, a crystallization inhibitor.

More preferably, this invention provides for a method of preventing or interrupting the transmission of mosquitoes and mosquito-borne diseases wherein, for example, the spot-on or pour-on formulation comprises:

(a) an effective amount of a compound of formula (I) wherein
$R_1$ is a halogen atom, CN or methyl;
$R_2$ is $S(O)_n R_3$ or 4,5-dicyanoimidazol-2-yl or haloalkyl;
$R_3$ is $C_1$-$C_6$-alkyl or $C_1$-$C_6$-haloalkyl;

R$_4$ represents a hydrogen or halogen atom; or NR$_5$R$_6$, S(O)$_m$R$_7$, C(O)R$_7$ or C(O)OR$_7$, alkyl, haloalkyl or OR$_8$ or —N═C(R$_9$)(R$_{10}$);

R$_5$ and R$_6$ independently represent a hydrogen atom or a C$_1$-C$_6$ alkyl, C$_1$-C$_6$-haloalkyl, C(O)C$_1$-C$_6$-alkyl, S(O)$_r$-CF$_3$, C$_1$-C$_6$-acyl or C$_1$-C$_6$-alkoxycarbonyl; R$_5$ and R$_6$ together may combine to form a ring of 5 to 7 members, which may include one or two divalent heteroatoms selected from the group consisting of oxygen or sulphur;

R$_7$ represents a C$_1$-C$_6$-alkyl or C$_1$-C$_6$-haloalkyl;

R$_8$ represents a C$_1$-C$_6$-alkyl or C$_1$-C$_6$-haloalkyl or a hydrogen atom;

R$_9$ represents a C$_1$-C$_6$-alkyl or a hydrogen atom;

R$_{10}$ represents an optionally substituted phenyl or optionally substituted heteroaryl group wherein the substituents are selected from the group consisting of halogen, OH, —O—C$_1$-C$_6$ alkyl, —S—C$_1$-C$_6$-alkyl, cyano or C$_1$-C$_6$-alkyl;

R$_{11}$ and R$_{12}$, independently of one another represent hydrogen, halogen, CN or NO$_2$;

R$_{13}$ represents a halogen, C$_1$-C$_6$-haloalkyl, C$_1$-C$_6$-haloalkoxy, S(O)$_q$Cl$_3$ or SF$_5$ group; and, m, n, q and r independently of one another are 0, 1, or 2.

(b) the liquid carrier vehicle comprises a solvent and a cosolvent wherein the solvent is selected from the group consisting of acetone, acetonitrile, benzyl alcohol, butyl diglycol, dimethylacetamide, dimethylformamide, dipropylene glycol n-butyl ether, ethanol, isopropanol, methanol, ethylene glycol monoethyl ether, monomethylacetamide, dipropylene glycol monomethyl ether, liquid polyoxyethylene glycols, propylene glycol, 2-pyrrolidone, in particular N-methylpyrrolidone, diethylene glycol monoethyl ether, ethylene glycol, diethyl phthalate fatty acid esters, such as the diethyl ester or diisobutyl adipate, and a mixture of at least two of these solvents and the cosolvent is selected from the group consisting of absolute ethanol, isopropanol or methanol;

(c) a crystallization inhibitor selected from the group consisting of an anionic surfactant, a cationic surfactant, a non-ionic surfactant, an amine salt, an amphoteric surfactant or polyvinylpyrrolidone, polyvinyl alcohols, copolymers of vinyl acetate and vinylpyrrolidone, polyethylene glycols, benzyl alcohol, mannitol, glycerol, sorbitol, polyoxyethylenated sorbitan esters; lecithin, sodium carboxymethylcellulose, and acrylic derivatives, or a mixture of these crystallization inhibitors.

Especially preferred as spot-on formulations to be used in the inventive method are those wherein the 1-N-arylpyrazole derivative is a compound wherein the ring formed by the divalent alkylene substituent representing R$_5$ and R$_6$ and the nitrogen atom to which R$_5$ and R$_6$ are attached has 5, 6 or 7 members or wherein R$_1$ is CN, R$_3$ is C$_1$-C$_6$-haloalkyl, R$_4$ is NH$_2$, R$_{11}$ and R$_{12}$ are, independently of one another, hydrogen or halogen and R$_{13}$ is C$_1$-C$_6$-haloalkyl.

Most especially preferred are formulations, including spot-on and pour-on compositions which are to be used in the inventive method, comprising:

(A) 5-amino-3-cyano-1-(2,6-dichloro-4-trifluoromethylphenyl)-4-trifluoromethylsulfinylpyrazole; or (B) 1-N-phenylpyrazole derivative of the formula:

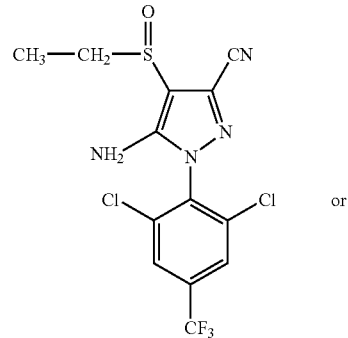

(I-A)

or

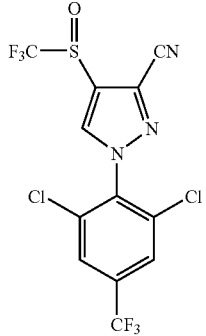

(I-B)

Other 1-N-arylpyrazole derivatives to be used in the formulation to the invention method which are preferred are those of the formula (II)

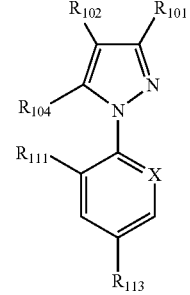

(II)

wherein:

R$_{101}$ is cyano, —C(O)alkyl, C(S)NH$_2$, alkyl, haloalkyl, C(═NOH)NH$_2$ or C(═NNH$_2$)NH$_2$;

R$_{102}$ is S(O)$_n$R$_{103}$, alkenyl, haloalkenyl, cycloalkyl, halocycloalkyl or alkynyl;

R$_{103}$ is alkyl, alkenyl, alkynyl, haloalkyl, haloalkenyl or haloalkynyl;

R$_{104}$ is —N═C(R$_{105}$)—Z—R$_{106}$, —N═C(R$_{105}$)—N(R$_{107}$)—R$_{108}$; or —N(R$_{109}$)—C(R$_{105}$)═NR$_{106}$;

R$_{105}$ is hydrogen; alkyl; or alkyl substituted by halogen, alkoxy, haloalkoxy or —S(O)$_m$R$_{105}$;

$R_{106}$ and $R_{107}$ each independently represent hydrogen, alkyl, alkenyl or alkynyl, or alkyl substituted by one or more halogen, alkoxy, haloalkoxy, amino, alkylamino, dialkylamino, cyano or —S(O)$_m$R$_{115}$; or alkyl substituted by phenyl or pyridyl each of which is optionally substituted with one or more groups selected from halogen, nitro and alkyl group; or $R_{107}$ and $R_{108}$ may form together with the nitrogen to which they are attached a 3- to 7-membered ring which may additionally contain one or more heteroatoms selected from oxygen, nitrogen or sulfur;

$R_{108}$ is alkoxy, haloalkoxy, amino, alkylamino, dialkylamino, —C(O) $R_{114}$ or —S(O)$_t$R$_{110}$;

$R_{109}$, $R_{110}$ and $R_{114}$ are alkyl or haloalkyl;

$R_{111}$ and $R_{112}$ are independently selected from halogen, hydrogen, CN and NO$_2$ $R_{113}$ is selected from halogen, haloalkyl, haloalkoxy, —S(O)$_q$CF$_3$, and —SF$_5$;

$R_{115}$ is alkyl or haloalkyl;

X is selected from nitrogen and C—$R_{112}$;

Z is O, S(O)$_{a'}$; or NR$_{107}$;

a', m', n' and q' are independently selected from 0, 1, and 2; and t' is 0, 1 or 2; and veterinarily acceptable salts thereof.

Another preferred 1-N-arylpyrazole derivatives to be used in the method of the present invention are those compounds of formula (III):

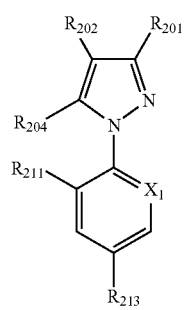

(III)

wherein:

$R_{201}$ is cyano, C(O)alkyl, C(S)NH$_2$, alkyl, C(=NOH)NH$_2$ or C(=NNH$_2$)NH$_2$;

$R_{202}$ is S(O)$_n$R$_{203}$, alkenyl, haloalkenyl, cycloalkyl, halocycloalkyl or alkynyl;

$R_{203}$ is alkyl, alkenyl, alkynyl, haloalkyl, haloalkenyl or haloalkynyl;

$R_{204}$ is —N(R$_{205}$)C(O)CR$_{206}$R$_{207}$R$_{208}$, —N(R$_{205}$)C(O)aryl, or —N(R$_{205}$)C(O)OR$_{207}$;

$R_{205}$ is alkyl, haloalkyl, cycloalkyl, halocycloalkyl, cycloalkylalkyl, halocycloalkylalkyl, alkoxyalkyl, haloalkoxyalkyl, alkenyl, haloalkenyl, alkynyl, haloalkynyl;

$R_{206}$ is hydrogen, halogen, alkoxy, haloalkoxy, alkoxyalkyl, haloalkoxyalkyl, formyloxy, alkylcarbonyloxy, haloalkylcarbonyloxy, alkylthio, haloalkylthio, alkylsulfinyl, haloalkylsulfinyl, alkylsulfonyl, haloalkylsulfonyl, alkylamino, dialkylamino, haloalkylamino, di(haloalkyl)amino, cycloalkyloxy, halocycloalkyloxy, alkoxyalkoxy, haloalkoxyalkoxy, alkoxyalkoxyalkoxy, aryloxy, or arylalkoxy;

$R_{207}$ and $R_{208}$ are independently hydrogen, alkyl, haloalkyl, cycloalkyl, or halocycloalkyl; or $R_{207}$ and $R_{208}$ may form together with the carbon to which they are attached a 3- to 7-membered ring which additionally may contain one or more heteroatoms selected from nitrogen, oxygen and sulfur;

$X_1$ is selected from nitrogen and C—$R_{212}$;

$R_{211}$ and $R_{212}$ are independently selected from halogen, hydrogen, CN and NO$_2$;

$R_{213}$ is selected from halogen, haloalkyl, haloalkoxy, —S(O)$_k$CF$_3$, and —SF$_5$;

and h and k are independently selected from 0, 1, and 2;

and veterinarily acceptable carrier, excipients and salts thereof.

A preferred class of compounds of formula (II) for use in the inventive method are those wherein:

$R_{101}$ is cyano or alkyl;

$R_{102}$ is S(O)$_n$R$_{103}$;

$R_{103}$ is alkyl or haloalkyl;

$R_{104}$ is —N=C(R$_{105}$)—Z—R$_{106}$;

$R_{105}$ is hydrogen, alkyl or haloalkyl;

Z is O, S(O)$_{a'}$; or NR$_{107}$;

$R_{106}$ and $R_{107}$ are independently selected from hydrogen and unsubstituted or substituted alkyl; or $R_{106}$ and $R_{107}$ may form together with the nitrogen to which they are attached a 3- to 7-membered ring which may additionally contain one or more heteroatoms selected from oxygen, nitrogen or sulfur; X is selected from nitrogen and C—$R_{112}$;

$R_{111}$ and $R_{112}$ are independently selected from halogen, hydrogen, CN and NO$_2$;

$R_{113}$ is selected from halogen, haloalkyl, haloalkoxy, —S(O)$_q$CF$_3$, and —SF$_5$;

a', n' and q' are independently selected from 0, 1, and 2.

Preferably $R_{106}$ is alkyl which is substituted by one or more halogen, alkoxy, haloalkoxy, amino, alkylamino, dialkylamino, sulfide, sulfoxide, sulfone, or phenyl or pyridyl moieties of which each phenyl or pyridyl moiety is optionally substituted with one or more groups selected from halo, nitro, and alkyl.

Preferably the compound useful in the method of the invention has one or more of the following features:

$R_{101}$ is cyano;

$R_{104}$ is —N=C(R$_{105}$)—Z—R$_{106}$ and Z is —NR$_{107}$;

X is C—$R_{112}$; $R_{111}$ and $R_{112}$ represent a chlorine atom; and $R_{113}$ is CF$_3$, OCF$_3$, or —SF$_5$;

$R_{112}$ is —S(O)$_n$CF$_3$ and n is 0, 1, or 2.

A further preferred class of compounds to be used in the inventive methods or approaches are those of formula II wherein:

$R_{101}$ is cyano or alkyl; $R_{104}$ is —N=C(R$_{105}$)—Z—R$_{106}$; and $R_{105}$ is hydrogen or C$_1$-C$_3$ alkyl.

The compounds of formula (II), preferably have one or more of the following features:

$R_{101}$ is cyano or methyl;

$R_{103}$ is halomethyl (preferably CF$_3$);

$R_{111}$ and $R_{112}$ each independently represent a halogen atom;

X is C—$R_{112}$;

$R_{113}$ is haloalkyl (preferably CF$_3$ haloalkoxy (preferably OCF$_3$), or —SF$_5$; or n' is 0, 1 or 2 (preferably 0 or 1).

A further preferred class of compounds of formula (II) for use in the control of parasites in animals are those wherein:

$R_{101}$ is cyano;

$R_{102}$ is S(O)$_n$R$_{103}$;

$R_{103}$ is halomethyl;

$R_{104}$ is —N=C(R$_{105}$)—Z—R$_{106}$;

Z is NR$_{107}$;

$R_{105}$ is hydrogen or alkyl;

$R_{106}$ and $R_{107}$ each independently represent hydrogen, alkyl, alkenyl or alkynyl; or alkyl substituted by one or more halogen, alkoxy, haloalkoxy, amino, alkylamino, dialkylamino, cyano or —S(O)$_m$R$_{15}$; or alkyl substituted by phenyl or pyridyl which rings are optionally substituted with one or more groups selected from halogen, nitro and alkyl;

X is selected from nitrogen and C—$R_{112}$;

$R_{106}$ and $R_{112}$ each independently represent a halogen atom; $R_{113}$ is selected from haloalkyl, haloalkoxy and —SF$_5$; $R_{115}$ is alkyl or haloalkyl; and m' and n' are independently selected from 0, 1, and 2.

A further preferred class of compounds of formula (II) is that wherein:

$R_{101}$ is cyano;
$R_{102}$ is S(O)$_n$CF$_3$;
$R_{104}$ is —N═C($R_{105}$)—Z—$R_{106}$ or —N═C($R_{105}$)—N($R_{107}$)—$R_{108}$;
Z is NR$_{107}$;
$R_{105}$ is hydrogen or alkyl;
$R_{106}$ and $R_{107}$ each independently represent hydrogen, alkyl, alkenyl or alkynyl; or alkyl substituted by one or more halogen, alkoxy, haloalkoxy, amino, alkylamino, dialkylamino, cyano or —S(O)R$_{115}$; or methyl substituted by phenyl or pyridyl which rings are optionally substituted with one or more groups selected from halogen, nitro and alkyl;
$R_{108}$ is alkoxy, haloalkoxy, amino, alkylamino, dialkylamino or —S(O)$_t$R$_{110}$;
X is selected from nitrogen and C—$R_{112}$;
$R_{109}$, $R_{110}$ and $R_{114}$ independently represent alkyl or haloalkyl;
$R_{111}$ and $R_{112}$ each represent a chlorine atom;
$R_{113}$ is CF$_3$ or —SF$_5$; and
m' and n' are 0, 1 or 2; and t' is 0 or 2.

A further preferred class of compounds of formula (II) are those wherein:

$R_{101}$ is cyano;
$R_{102}$ is S(O)$_{n1}$CF$_3$;
$R_{104}$ is —N═C($R_{105}$)—Z—$R_{106}$;
Z is NR$_{107}$;
$R_{105}$ is hydrogen or methyl;
$R_{106}$ and $R_{107}$ each independently represent hydrogen, alkyl, alkenyl or alkynyl; or alkyl substituted by one or more halogen, alkoxy, haloalkoxy, amino, alkylamino, dialkylamino, cyano or —S(O)$_m$R$_{115}$; or alkyl substituted by phenyl or pyridyl which rings are optionally substituted with one or more groups selected from halogen, nitro and alkyl;
X is C—$R_{112}$
$R_{111}$ and $R_{112}$ each represent a chlorine atom;
$R_{113}$ is CF$_3$ or —SF$_5$;
m' is zero, one or two; and
n' is 0 or 1.

A further preferred class of compounds of formula (II) is those wherein:

$R_{101}$ is cyano;
$R_{102}$ is S(O)$_n$CF$_3$;
$R_{104}$ is —N═C($R_{105}$)—Z—$R_{106}$;
Z is NR$_{107}$;
$R_{105}$ and $R_{107}$ each represent a hydrogen atom;
$R_{106}$ is alkyl or haloalkyl;
X is C—$R_{112}$;
$R_{111}$ and $R_{112}$ each represent a chlorine atom;
$R_{113}$ is CF$_3$ or —SF$_5$; and
n' is 0.

Compounds of formula (III) which are preferred according to the present invention are those wherein:

$R_{201}$ is cyano;
$R_{202}$ is S(O)$_h$R$_{203}$;
$R_{203}$ is alkyl or haloalkyl;
$R_{204}$ is —N($R_{205}$)C(O)CR$_{206}$R$_{207}$R$_{208}$;
$R_{205}$ is alkyl, haloalkyl, cycloalkyl, cycloalkylalkyl and halocycloalkylalkyl;
$R_{206}$ is alkoxy, haloalkoxy, or hydrogen;
$R_{207}$ and $R_{208}$ are independently hydrogen, alkyl, or haloalkyl; or
$R_{207}$ and $R_{208}$ may form together with the carbon to which they are attached to a 3- to 7-membered ring which additionally may contain one or more heteroatoms selected from nitrogen, oxygen and sulfur;
$X_1$ is selected from nitrogen and C—$R_{212}$;
$R_{211}$ and $R_{212}$ are independently selected from halogen, hydrogen, CN and NO$_2$;
$R_{213}$ is selected from halogen, haloalkyl, haloalkoxy, —S(O)$_k$CF$_3$, and —SF$_5$;
and
h and k are independently selected from 0, 1, and 2.

A preferred group of compounds of formula (III) is that wherein the ring which is formed by $R_{207}$ and $R_{208}$ contains one or more heteroatoms, more preferably one oxygen atom.

The compounds of formula (III) of the present invention preferably have one or more of the following features:

$R_{201}$ is cyano;
$R_{203}$ is halomethyl, preferably CF$_3$;
$R_{211}$ and $R_{212}$ are independently halogen;
$X_1$ is C—$R_{212}$;
$R_{213}$ is haloalkyl, haloalkoxy or —SF$_5$; or
h is 0 or 1, or 2, preferably 0 or 1.

A preferred class of compounds that wherein $R_{204}$ is N($R_{205}$)C(O)CR$_{206}$R$_{207}$R$_{208}$.

Another preferred class of compounds that wherein $R_{204}$ is N($R_{205}$)C(O)aryl.

Another preferred class of compounds that wherein $R_{204}$ is N($R_{205}$)C(O)OR$_{207}$.

Preferably $R_{205}$ is C$_1$-C$_4$ alkyl, more preferably C$_1$-C$_2$ alkyl, most preferably methyl.

Preferably $R_{206}$ is alkoxy, most preferably methoxy, ethoxy or propoxy.

Preferably $R_{207}$ and $R_{208}$ are both hydrogen.

Another especially preferred group of 1-N-arylpyrazole derivative is 4-thiocarbonylpyrazole derivatives of the formula:

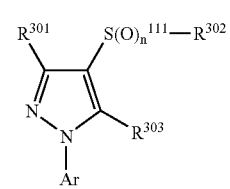

(IV)

in which $R^{301}$ is H$_2$N—C(S)—,
$R^{302}$ is halogenoalkyl, halogenoalkenyl or halogenoalkynyl,
$R^{303}$ is hydrogen, amino or one of the following groups:

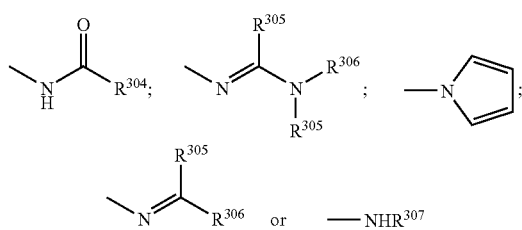

where
- $R^{304}$ represents alkyl, halogenoalkyl, alkoxyalkyl or in each case optionally substituted phenyl or pyridyl,
- $R^{305}$ represents hydrogen or alkyl,
- $R^{306}$ represents hydrogen, alkyl or in each case optionally substituted phenyl or pyridyl and
- $R^{307}$ represents alkyl, alkenyl, alkinyl, formyl, alkylcarbonyl, halogenoalkylcarbonyl or alkoxycarbonyl;
- Ar represents in each case optionally substituted phenyl or pyridyl and n represents a number 0, 1 or 2.

Especially preferred derivatives of formula (W) are those wherein
- $R^{301}$ represents $H_2N\text{—}C(S)\text{—}$;
- $R^{302}$ preferably represents $(C_1\text{-}C_6)$-halogenoalkyl having 1 to 12 halogen atoms; $(C_2\text{-}C_6)$-halogenoalkenyl having 1 to 8 halogen atoms or $(C_1\text{-}C_6)$-halogenoalkinyl having 1 to 6 halogen atoms;
- $R^{303}$ preferably represents hydrogen, amino or one of the following groups:

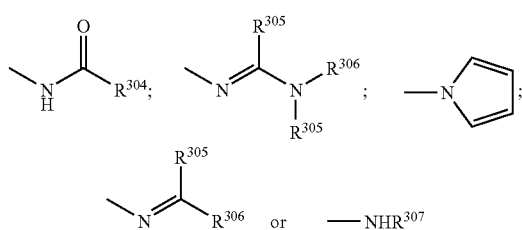

wherein:
- $R^{304}$ represents $(C_1\text{-}C_6)$-alkyl, $(C_1\text{-}C_6)$-halogenoalkyl having 1 to 3 halogen atoms, $(C_1\text{-}C_6)$-alkoxy-$(C_1\text{-}C_6)$-alkyl, or represents phenyl or pyridyl, each of which is optionally monosubstituted to trisubstituted by identical or different substituents from the group consisting of cyano, nitro, halogen, $C_1\text{-}C_6$-alkyl, $C_1\text{-}C_6$-alkoxy, $C_1\text{-}C_6$-alkylthio, $C_1\text{-}C_4$-halogenoalkyl, $C_1\text{-}C_4$ halogenoalkoxy or $C_1\text{-}C_4$-halogenoalkylthio having in each case 1 to 5 halogen atoms,
- $R^{305}$ represents hydrogen or $(C_1\text{-}C_6)$-alkyl,
- $R^{306}$ represents hydrogen, $(C_1\text{-}C_6)$-alkyl, phenyl which is optionally monosubstituted to trisubstituted by identical or different substituents from the group consisting of cyano, nitro, halogen, $C_1\text{-}C_6$-alkyl, $C_1\text{-}C_6$-alkoxy, $C_1\text{-}C_6$-alkylthio, $C_1\text{-}C_4$-halogenoalkyl, $C_1\text{-}C_4$-halogenoalkoxy or $C_1\text{-}C_4$-halogenoalkylthio having in each case 1 to 5 halogen atoms or hydroxyl, or represents pyridyl which is substituted by cyano, nitro, halogen, $C_1\text{-}C_6$-alkyl, $C_1\text{-}C_6$-alkoxy, $C_1\text{-}C_6$-alkylthio, $C_1\text{-}C_4$-halogenoalkyl, $C_1\text{-}C_4$-halogenoalkoxy or $C_1\text{-}C_4$-halogenoalkylthio having in each case 1 to 5 halogen atoms, and
- $R^{307}$ represents $(C_1\text{-}C_6)$-alkyl, $(C_2\text{-}C_6)$-alkenyl, $(C_2\text{-}C_6)$-alkynyl, formyl, $(C_1\text{-}C_6)$-alkylcarbonyl, $(C_1\text{-}C_6)$-halogenoalkylcarbonyl having 1 to 6 halogen atoms or $(C_1\text{-}C_6)$-alkoxycarbonyl;
- Ar preferably represents phenyl or pyridyl, each of which is optionally monosubstituted to trisubstituted by identical or different substituents from the group consisting of halogen halogeno$(C_1\text{-}C_6)$alkyl, halogeno$(C_1\text{-}C_6)$alkylthio, halogeno$(C_1\text{-}C_6)$alkoxy, $(C_1\text{-}C_6)$alkoxy, methoxy, hydrazine, $(C_1\text{-}C_6)$-dialkylhydrazino, amino, $(C_1\text{-}C_6)$alkylamino, di$(C_1\text{-}C_6)$alkylamino, $(C_1\text{-}C_6)$ alkylimino, cyano, $(C_1\text{-}C_6)$alkylthio or the group

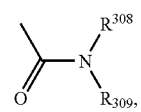

in which
- $R^{308}$ and $R^{309}$ are identical or different and represent hydrogen or $(C_1\text{-}C_6)$-alkyl
- $n^{111}$ preferably represents a number 0, 1 or 2.
- $R^{301}$ represents $H_2N\text{—}C(S)\text{—}$;
- $R^{302}$ particularly preferably represents $(C_1\text{-}C_4)$-halogenoalkyl having 1 or 9 identical or different halogen atoms from the group consisting of fluorine, chlorine and bromine, $(C_2\text{-}C_4)$-halogenoalkenyl having 1 to 5 identical or different halogen atoms from the group consisting of fluorine, chlorine or bromine or $(C_2\text{-}C_4)$-halogenoalkynyl having 1 to 5 identical or different halogen atoms from the group consisting of fluorine, chlorine and bromine;
- $R^{303}$ especially preferably represents hydrogen, amino or one of the following groups:

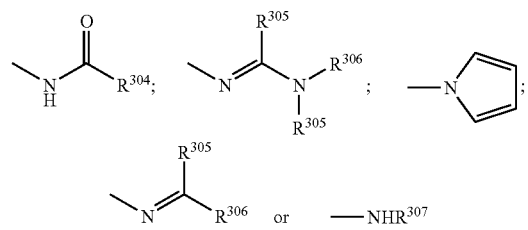

where
- $R^{304}$ represents $(C_1\text{-}C_4)$-alkyl, $(C_1\text{-}C_4)$-halogenoalkyl having 1-3 halogen atoms, $(C_1\text{-}C_4)$-alkoxy$(C_1\text{-}C_2)$-alkyl, or phenyl which is optionally monosubstituted to trisubstituted by identical or different substituents from the group consisting of hydroxyl, cyano, nitro, halogen, $C_1\text{-}C_4$-alkyl, $C_1\text{-}C_4$-alkoxy, $(C_1\text{-}C_2)$-halogenoalkyl, $C_1\text{-}C_2$-halogenoalkoxy or $C_1\text{-}C_2$-halogenoalkylthio having in each case 1 to 3 halogen atoms,
- $R^{305}$ represents hydrogen or $(C_1\text{-}C_4)$-alkyl,
- $R^{306}$ represents hydrogen, $(C_1\text{-}C_4)$-alkyl or phenyl which is optionally monosubstituted or disubstituted by identical or different substituents from the group consisting of hydroxyl, cyano, nitro, halogen, $C_1\text{-}C_4$-alkyl, $C_1\text{-}C_4$-alkoxy, $C_1\text{-}C_2$-halogenoalkyl, $C_1\text{-}C_2$ halogenoalkoxy or $C_1\text{-}C_2$ halogenoalkylthio having in each case 1 to 3 halogen atoms, in particular 4-hydroxy-3-methoxyphenyl, and $R^{307}$ represents $(C_1-C_4)$-alkyl, $(C_2-C_4)$-alkenyl, $(C_2-C_4)$-alkynyl, formyl, $(C_1-C_4)$-alkylcarbonyl, $(C_1-C_4,)$-halogenoalkylcarbonyl having 1 to 5 identical or different halogen atoms from the group consisting of fluorine, chlorine or bromine or $(C_1-C_4)$-alkoxycarbonyl;

Ar especially preferably represents phenyl or pyridyl, each of which is optionally monosubstituted to trisubstituted by identical or different substituents from the group consisting of fluorine, chlorine, trifluoromethyl, trifluoromethylthio, trifluoromethoxy, methoxy, hydrazine, dimethylhydrazino, amino, methylamino, dimethylamino, iminomethyl, cyano, methylthio or the group

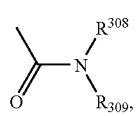

where $R^{308}$ and $R^{309}$ are identical or different and represent hydrogen or $(C_1-C_4)$-alkyl;

$n^{111}$ especially preferably represents a number 0, 1 or 2.

Compounds of formula (IV) which are most preferably preferred are those where $R^{301}$ represents $H_2N-C(S)-$;

$R^{302}$ most preferably represents one of the following groups: $-CF_3$, $-CHF_2-CF_2-CH_3-CF_3-CHF_2$, $-CF_2CHFCl$, $-CH_2-CF_3$, $-CH_2CF_2Cl$, $-CH_2-CF_2-CHF_2$, $-CF_2-CFCl-CF_3$, $-C(Cl)(CF_3)-CF_2Cl$, $-C(Cl)(CF_3)-CHCl-CF_3$, $-C(CF_3)=CCl_2$ $R^{303}$ most preferably represents hydrogen, amino or one of the groups: $-NH-CO-CH_3$, $-NH-CO-C_2H_5$, $-N=CH-NH_2$, $-N=C(CH_3)-NH_2$, $-N=CH-N(CH_3)_2$, $-N=C(CH_3)-N(CH_3)_2$,

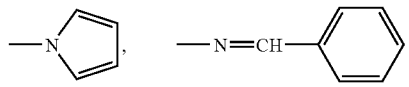

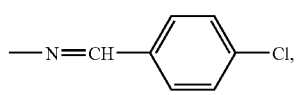

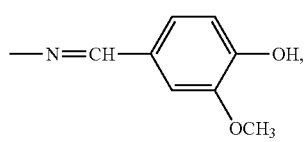

$-NHC_2H_5$ or $-NH-CH_2-CH=CH_2$.

Ar most preferably represents (1) phenyl which is disubstituted or trisubstituted by identical or different substituents, where fluorine or chlorine occupies the 2-position, trifluoromethyl the 4-position and fluorine, chlorine, cyano, methoxy, methylthio, trifluoromethyl, trifluoromethoxy, trifluoromethylthio or hydrazino the 6-position; or (2) a 2-pyridyl substituent which is substituted in the 4-position by trifluoromethyl and in the 6-position by fluorine or chlorine.

$n^{111}$ most preferably represents one of the integers 0, 1 or 2. A most especially preferred compound is one wherein $R^{302}$ is $-CF_3$, $R^{303}$ is amino, Ar is a phenyl which is trisubstituted and the substituents are a 2-position chloro group, a 4-position trifluoromethyl group and a 6-position chloro group, and $n^{111}$ is 1. Especially preferred compounds are those of the formulae.

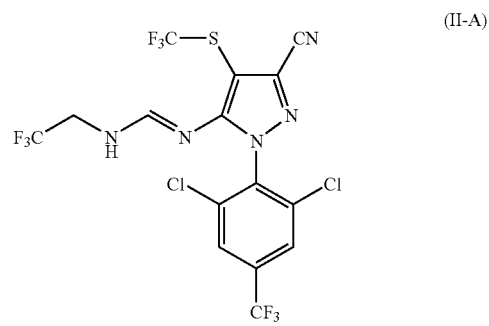

(II-A)

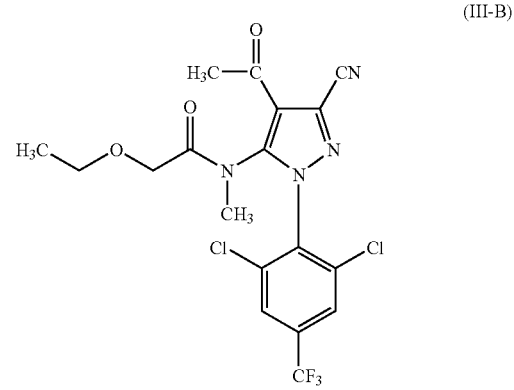

(III-B)

Other preferred 1-N-arylpyrazoles include the following compounds:

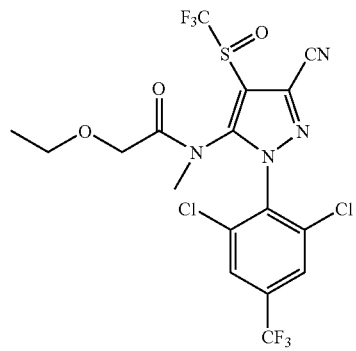

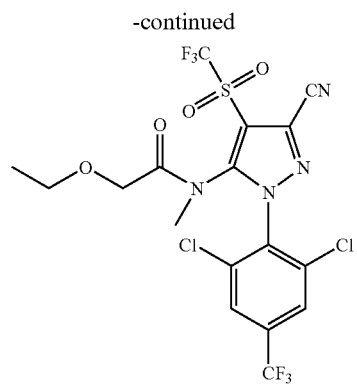
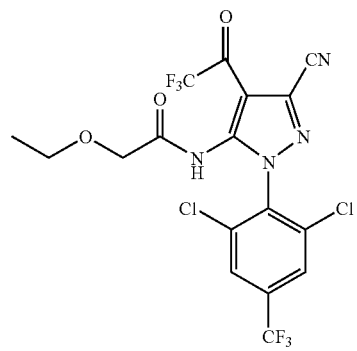
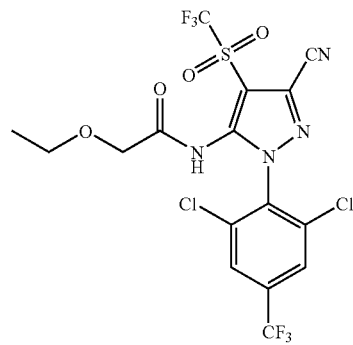
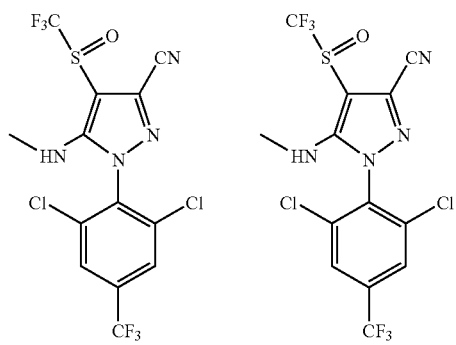
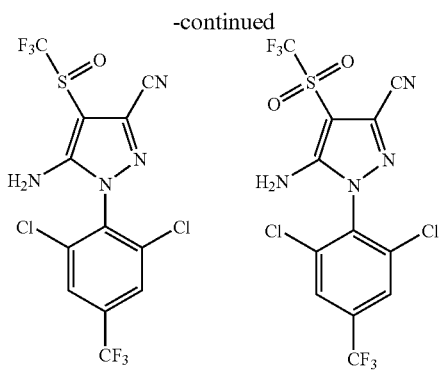
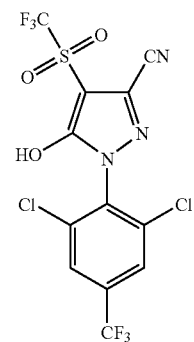
Especially preferred 1-N-arylpyrazoles derivative in addition to fipronil include fipronil thio
and fipronil sulfone
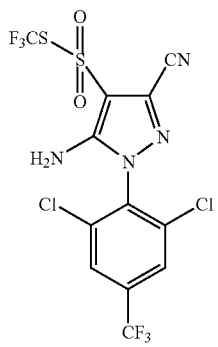

In addition to the patent discussing 1-N-arylpyrazoles derivatives discussed previously, one skilled in the art could make these compounds by adopting procedures described in DE 19928155, DE 19853560, WO 2000031043, DE 19650197, WO 9824769, U.S. Pat. No. 6,265,430, US 2001007876, all of which are herein incorporated by reference.

Insect growth regulating (IGR) compounds are another class of insecticides or acaricides, which are provided for in the bait formulations in this invention. Compounds belonging to this group are well known to the practitioner and represent a wide range of different chemical classes. These compounds all act by interfering with the development or growth of the insect pests. Compounds with an ovicidal and/or larvicidal effect on the immature stages of various ectoparasites are already known, for example from U.S. Pat. No. 5,439,924. Among these compounds described are those IGR compounds which act either by blocking the development of the immature stages (eggs and larvae) into adult stages, or by inhibiting the synthesis of chitin. Insect growth regulators are described, for example, in U.S. Pat. Nos. 3,748,356; 3,818,047; 4,225,598; 4,798,837; and 4,751,225, as well as in EP 179,022 or U.K. 2,140,010. French Patent No. A-2,713,889 generally describes an IGR combination comprising at least one compound with juvenile hormone activity and chitin synthesis inhibitors, with at least one of three N-arylpyrazole compounds, in particular fipronil, to control many harmful insects belonging to very varied orders.

Examples of IGR compounds which may be used in this invention include compounds which mimic juvenile hormones, in particular:

azadirchtin—Agridyne
  diofenolan (Ciba Geigy now Novartis)
  fenoxycarb (Ciba Geigy now Novartis)
  hydroprene (Sandoz now Novartis)
  kinoprene (Sandoz now Novartis)
  methoprene (Sandoz now Novartis)
  pyriproxyfen (Sumitomo/Mgk)
  tetrahydroazadirachtin (Agridyne)
  4-chloro-2-(2-chloro-2-methylpropyl)-5-(6-iodo-3-pyridylmethoxy)pyridizin-3(2H)-one and chitin-synthesis inhibitors, in particular:

chlorfluazuron (Ishihara Sangyo)
  cyromazine (Ciba Geigy now Novartis)
  diflubenzuron (Solvay Duphar)
  fluazuron (Ciba Geigy now Novartis)
  flucycloxuron (Solvay Duphar)
  flufenoxuron (Cyanamid)
  hexaflumuron (Dow Elanco)
  lufenuron (Ciba Geigy now Novartis)
  tebufenozide (Rohm & Haas)
  teflubenzuron (Cyanamid)
  triflumuron (Bayer).

These compounds are defined by their international common name (The Pesticide Manual, 10$^{th}$ edition, 1994, Ed. Clive Tomlin, Great Britain).

Chitin-synthesis inhibitors also include compounds such as 1-(2,6-difluorobenzoyl)-3-(2-fluoro-4-((trifluoromethyl)) phenylurea, 1-(2,6-difluorobenzoyl)-3-(2-fluoro-4-(1,1,2,2-tetrafluoroethoxy))phenylurea and 1-(2,6-difluorobenzoyl)-3-(2-fluoro-4-trifluoro-methyl)phenylurea. Novaluron (Isagro, Italian company) is also an example of an IGR compound.

Preferred IGR compounds include methoprenes, pyriproxyfens, hydroprene, cyromazine, lufenuron, 1-(2,6-difluorobenzoyl)-3-(2-fluoro-4-(trifluoromethyl)phenylurea and novaluron.

The alkyl groups of the definition of the compounds (1) of the formula (I) generally comprise from 1 to 6 carbon atoms. The ring formed by $R_5$ and $R_6$ and the nitrogen atom to which they are attached is generally a 5-, 6- or 7-membered ring.

Unless otherwise specified, alkyl and alkoxy groups are generally lower alkyl and alkoxy groups, that is having from one to six carbon atoms, preferably from one to four carbon atoms. Generally, the haloalkyl, haloalkoxy and alkylamino groups have from one to four carbon atoms. The haloalkyl and haloalkoxy groups can bear one or more halogen atoms; preferred groups of this type include —$CF_3$ and —$OCF_3$. Cycloalkyl groups generally have from 3 to 6 carbon atoms, preferably from 3 to 5 carbon atoms, and may be substituted by one or more halogen atoms. Alkenyl, haloalkenyl, alkynyl, and haloalkynyl groups generally contain from 3 to 5 carbon atoms. By the term aryl is generally meant phenyl, pyridyl, furyl, and thiophenyl, each of which is optionally substituted by one or more halogen, alkyl, haloalkyl, nitro, alkoxy, haloalkoxy, hydroxy, amino, alkylamino or dialkylamino. In compounds of formulae (1) to (III), by the term substituted alkyl is meant alkyl which is substituted by, for example, one or more halogen, alkoxy, haloalkoxy, amino, alkylamino, dialkylamino, cyano or —$S(O)_m R_{115}$; or alkyl substituted by phenyl or pyridyl each of which is optionally substituted with one or more groups selected from halogen, nitro and alkyl; wherein $R_{115}$ is alkyl or haloalkyl and m is zero, one or two. Preferably in compounds of formula (I), alkyl groups are generally substituted by from one to five halogen atoms, preferably from one to three halogen atoms. Chlorine and fluorine atoms are preferred.

Compounds of formula wherein $R_{104}$ is —N=C($R_{105}$)—Z—$R_{106}$, Z is $NR_{107}$ and $R_{106}$ represent a hydrogen atom may exist as the tautomeric double bond isomer form —NH—C($R_{105}$)=N—$R_{107}$. It is to be understood that both such forms are embraced by the present invention.

In compounds of formula (III) the following examples of substituents are provided:

An example of cycloalkylalkyl is cyclopropylmethyl; an example of cycloalkoxy is cyclopropyloxy;

An example of alkoxyalkyl is $CH_3OCH_2$—;

An example of alkoxyalkoxy is $CH_3OCH_2O$—;

An example of alkoxyalkoxyalkoxy is $CH_3OCH_2OCH_2O$—;

An example of aryloxy is the phenoxy group; and

An example of the arylalkoxy group is benzyloxy or 2-phenylethoxy.

Generally, in dialkylamino or di(haloalkyl)amino groups, the alkyl and haloalkyl groups on nitrogen may be chosen independently of one another.

A preferred class of compounds of formula (I) comprises the compounds such that $R_1$ is CN, $R_3$ is haloalkyl, $R_4$ is $NH_2$, $R_{11}$ and $R_{12}$ are, independently of one another, a halogen atom and $R_{13}$ is haloalkyl. Preferably still, X is C—$R_{12}$. A compound of formula (I) which is very particularly preferred in the invention is 5-amino-3-cyano-1-(2,6-dichloro-4-trifluoromethylphenyl)-4-trifluoromethylsulfinylpyrazole or fipronil.

Compounds of formulae (I)-(III) can be prepared according to one or other of the processes described in Patent Applications WO 87/3781, 93/6089 and 94/21606, and 00/59862 or European Patent Application 295,117 or any other process coming within the competence of a person skilled in the art who is an expert in chemical synthesis. For the chemical preparation of the products of the invention, a person skilled in the art is regarded as having at his disposal, inter alia, the entire contents of "Chemical Abstracts" and of the documents which are cited therein.

Administration of the inventive formulation may be intermittent in time and may be administered daily, weekly, biweekly, monthly, bimonthly, quarterly, or even for longer durations of time. The time period between treatments depends upon factors such as the parasite(s) being treated, the degree of infestation, the type of mammal or bird and the environment where it resides. It is well within the skill level of the practitioner to determine a specific administration period for a particular situation. This invention contemplates a method for combating mosquitoes in an environment in which the animal is subjected to strong mosquito pressure where the administration is at a frequency far below a daily administration in this case. For example, it is preferable for the treatment according to the invention to be carried out monthly on dogs and on cats and or birds.

Spot-on and pour-on formulations may be prepared by dissolving the active ingredients into the pharmaceutically or veterinary acceptable vehicle. Alternatively, the spot-on formulation can be prepared by encapsulation of the active ingredient to leave a residue of the therapeutic agent on the surface of the animal. These formulations will vary with regard to the weight of the therapeutic agent in the combination depending on the species of host animal to be treated, the severity and type of infection and the body weight of the host. The compounds may be administered continuously, particularly for prophylaxis, by known methods. Generally, a dose of from about 0.001 to about 10 mg per kg of body weight given as a single dose or in divided doses for a period of from 1 to 5 days will be satisfactory but, of course, there can be instance where higher or lower dosage ranges are indicated and such are within the scope of this invention. It is well within the routine skill of the practitioner to determine a particular dosing regimen for a specific host and parasite.

Preferably, a single formulation containing the 1-N-arylpyrazole derivative in a substantially liquid carrier and in a form which makes possible a single application, or an application repeated a small number of times, will be administered to the animal over a highly localized region of the animal, preferably between the two shoulders. Most preferably, this localized region has a surface area of less than 10 cm$^2$, especially between 5 and 10 cm$^2$ area. Remarkably, it has been discovered that such a formulation is highly effective against the mosquito, thereby preventing or interrupting the transmission of the mosquito-borne disease.

The treatment is preferably carried out so as to administer to the host, on a single occasion, a dose containing between about 0.001 and about 100 mg/kg of 1-N-arylpyrazole derivative and, in particular, a dose that is topically administered.

The amount of 1-N-arylpyrazole for birds and animals which are small in size is preferably greater than about 0.01 mg and in a particularly preferred way between about 1 and about 50 mg/kg of weight of animal.

It also may be preferable to use controlled-release formulations.

With regard to formulations which comprise both 1-N-arylpyrazole and IGR compounds, it is preferable to administer the two classes of compounds concomitantly and, most preferably, simultaneously.

Preferably, the treatment is carried out so as to administer to the animal a dose of from about 0.1 to about 40 and in particular from about 1 to about 20 mg/kg of 1-N-phenylpyrazole and a dose of from about 0.1 to about 40 and in particular about 1 to about 30 mg/kg of IGR compound.

The preferred doses are from about 5 to about 15 mg/kg of I-N-arylpyrazoles and from about 0.5 to about 15 mg/kg for the preferred IGR compounds, or about 10 to about 20 mg/kg for the other IGR compounds.

In another embodiment of the method according to the invention, the 1-N-arylpyrazoles and the IGR compounds may be applied in a distinct and separate manner over time. In this case, it is preferred to alternate the applications with an interval, for example of one month between two applications, the first application preferably being made with the 1-N-arylpyrazole.

It is understood that the dosage values which are thus indicated are average values which may vary within a wide range, since, in practice, a formulation having defined doses of 1-N-arylpyrazole-type derivative and of an IGR compound will be administered to animals having relatively different weights. Consequently, the doses actually applied are often smaller or larger by a factor which may be up to 2, 3 or 4 relative to the preferred dose, without entailing any toxic risk for the animal in the case of an overdose, and while at the same time retaining real efficacy, possibly of shorter duration, in the case of an underdose.

While not wishing to be bound by theory, it is believed that the invention spot-on formulation works by the dose dissolving in the natural oils of the host's skin, fur or feathers. From there, the therapeutic agent(s) distribute around the host's body through the sebaceous glands of the skin. The therapeutic agent also remains in the sebaceous glands. Thus, the glands provide a natural reservoir for the therapeutic agent which allows for the agent to be drained back out to the follicles to reapply itself to the skin and hair feathers. This, in turn, provides for longer time periods between applications as well as not having to re-administer the dose after the host becomes wet because of rain, baths, etc. Moreover, the inventive formulations have the further advantage in self-grooming animals of not being directly deposited on the skin or fur where the animals might orally ingest the therapeutic agent, thereby increasing the safety margin.

The spot-on formulations of the present invention provide for the topical administration of a concentrated solution, suspension, microemulsion or emulsion for intermittent application to a spot on the animal, generally between the two shoulders (solution of spot-on type). It has been discovered that the inventive formulations are especially active against parasites when the formulations are applied to mammals and birds, especially poultry, dogs, cats, sheep, pigs, cattle zebras, horses, donkeys, mice, chipmunks and tree squirrels. These formulations comprise a composition of an effective amount of compound (1) and/or IGR compound dissolved in a pharmaceutical or veterinary-acceptable carrier vehicle where a crystallization inhibitor is optionally present. The N-arylpyrazoles can advantageously be present in the formulations in a proportion of about 1 to about 20%, preferably of about 5 to about 15% (percentages as weight by volume=W/V). The liquid carrier vehicle comprises a pharmaceutically or veterinary acceptable organic solvent and optionally an organic cosolvent.

Also contemplated are the pharmaceutically or veterinary-acceptable acid or base salts, where applicable, of the active compounds provided for herein. The term "acid" contemplates all pharmaceutically or veterinary acceptable inorganic or organic acids. Inorganic acids include mineral acids such as hydrohalic acids, such as hydrobromic and hydrochloric acids, sulfuric acids, phosphoric acids and nitric acids. Organic acids include all pharmaceutically or veterinary-acceptable aliphatic, alicyclic and aromatic carboxylic acids, dicarboxylic acids, tricarboxylic acids and fatty acids. Preferred acids are straight chain or branched, saturated or unsaturated $C_1$-$C_{20}$ aliphatic carboxylic acids, which are optionally substituted by halogen or by hydroxyl groups, or $C_6$-$C_{12}$ aromatic carboxylic acids. Examples of such acids are carbonic acid, formic acid, fumaric acid, acetic acid, propionic acid, isopropionic acid, valeric acid, α-hydroxy acids, such as glycolic acid and lactic acid, chloroacetic acid, benzoic acid, methane sulfonic acid, and salicylic acid. Examples of dicarboxylic acids include oxalic acid, malic acid, succinic acid, tataric acid and maleic acid. An example of a tricarboxylic acid is citric acid. Fatty acids include all pharmaceutically or veterinary-acceptable saturated or unsaturated aliphatic or aromatic carboxylic acids having 4 to 24 carbon atoms. Examples include butyric acid, isobutyric acid, sec-butyric acid, lauric acid, palmitic acid, stearic acid, oleic acid, linoleic acid, linolenic acid, and phenylsteric acid. Other acids include gluconic acid, glycoheptonic acid and lactobionic acid.

The term "base" contemplates all pharmaceutically or veterinary acceptable inorganic or organic bases. Such bases include, for example, the alkali metal and alkaline earth metal salts, such as the lithium, sodium, potassium, magnesium or calcium salts. Organic bases include the common hydrocarbyl and heterocyclic amine salts, which include, for example, the morpholine and piperidine salts.

The organic solvent for the liquid carrier vehicle will preferably have a dielectric constant of between about 10 and about 35, preferably between about 20 and about 30, the content of this solvent in the overall composition preferably representing the remainder of 100% of the composition. It is well within the skill level of the practitioner to select a suitable solvent on the basis of these parameters.

The organic cosolvent for the liquid carrier vehicle will preferably have a boiling point of less than about 100° C., preferably of less than about 80° C., and will have a dielectric constant of between about 10 and about 40, preferably between about 20 and about 30; this cosolvent can advantageously be present in the composition according to a weight/weight (W/W) ratio with respect to the solvent of between about 1/15 and about 1/2; the cosolvent is volatile in order to act in particular as drying promoter and is miscible with water and/or with the solvent. Again, it is well within the skill level of the practitioner to select a suitable solvent on the basis of these parameters.

The organic solvent for the liquid carrier includes the commonly acceptable organic solvents known in the formulation art. These solvents may be found, for example, in Remington Pharmaceutical Science, 16$^{th}$ Edition (1986). These solvents include, for example, acetone, ethyl acetate, methanol, ethanol, isopropanol, dimethylformamide, dichloromethane or diethylene glycol monoethyl ether (Transcutol). These solvents can be supplemented by various excipients according to the nature of the desired phases, such as $C_8$-$C_{10}$ caprylic/capric triglyceride a hydrogenated or fractionated coconut oil (Estasan or Miglyol 812), oleic acid or propylene glycol.

The liquid carrier may also comprise a microemulsion. Microemulsions are also well suited as the liquid carrier vehicle. Microemulsions are quaternary systems comprising an aqueous phase, an oily phase, a surfactant and a cosurfactant. They are translucent and isotropic liquids.

Microemulsions are composed of stable dispersions of microdroplets of the aqueous phase in the oily phase or conversely of microdroplets of the oily phase in the aqueous phase. The size of these microdroplets is less than 200 nm (1000 to 100,000 nm for emulsions). The interfacial film is composed of an alternation of surface-active (SA) and co-surface-active (Co-SA) molecules which, by lowering the interfacial tension, allows the microemulsion to be formed spontaneously.

The oily phase can in particular be formed from mineral or vegetable oils, from unsaturated polyglycosylated glycerides or from triglycerides, or alternatively from mixtures of such compounds. The oily phase preferably comprises triglycerides and more preferably medium-chain triglycerides, for example $C_8$-$C_{10}$ caprylic/capric triglyceride. The oily phase will represent, in particular, from about 2 to about 15% more, particularly from about 7 to about 10%, preferably from about 8 to about 9%, V/V of the microemulsion. Suitable oils for the oily phase are known in the art and are described, for example, in U.S. Pat. Nos. 6,036,394; 5,580,574; 6,174,540 and WO 97/37653, herein incorporated by reference.

The aqueous phase includes, for example, water or glycol derivatives, such as propylene glycol, glycol ethers, polyethylene glycols or glycerol. Propylene glycol, diethylene glycol monoethyl ether and dipropylene glycol monoethyl ether are especially preferred. Generally, the aqueous phase will represent a proportion from about 1 to about 4% V/V in the micro emulsion.

Surfactants for the microemulsion include diethylene glycol monoethyl ether, dipropylene glycol monomethyl ether, polyglycolysed $C_8$-$C_{10}$ glycerides or polyglyceryl-6 dioleate. In addition to these surfactants, the cosurfactants include short-chain alcohols, such as ethanol and propanol.

Some compounds are common to the three components discussed above, i.e., aqueous phase, surfactant and cosurfactant. However, it is well within the skill level of the practitioner to use different compounds for each component of the same formulation.

The cosurfactant to surfactant ratio will preferably be from about 1/7 to about 1/2. There will preferably be from about 25 to about 75% V/V of surfactant and from about 10 to about 55% V/V of cosurfactant in the microemulsion.

Likewise, the co-solvents are also well known to a practitioner in the formulation art. Preferred co-solvents are those which are promoters of drying and include, for example, absolute ethanol, isopropanol (2-propanol) or methanol.

The crystallization inhibitor can in particular be present in a proportion of about 1 to about 20% (W/V), preferably of about 5 to about 15%. The inhibitor preferably corresponds to the test in which 0.3 ml of a solution comprising 10% (W/V) of the compound of formula (I) in the liquid carrier and 10% of the inhibitor are deposited on a glass slide at 20° C. and allowed to stand for 24 hours. The slide is then observed with the naked eye. Acceptable inhibitors are those whose addition provides for few or no crystals, and in particular less than 10 crystals, preferably 0 crystals.

Although this is not preferred, the formulation can optionally comprise water, in particular in a proportion of 0 to about 30% (volume by volume V/V), in particular of 0 to about 5%.

The formulation can also comprise an antioxidizing agent intended to inhibit oxidation in air, this agent being particularly present in a proportion of about 0.005 to about 1% (W/V), preferably of about 0.01 to about 0.05%.

Crystallization inhibitors which can be used in the invention include:

polyvinylpyrrolidone, polyvinyl alcohols, copolymers of vinyl acetate and of vinylpyrrolidone, polyethylene glycols, benzyl alcohol, mannitol, glycerol, sorbitol or polyoxyethylenated esters of sorbitan; lecithin or sodium carboxymethylcellulose; or acrylic derivatives, such as methacrylates and others, anionic surfactants, such as alkaline stearates, in particular sodium, potassium or ammonium stearate; calcium stearate or triethanolamine stearate; sodium abietate; alkyl sulphates, in particular sodium lauryl sulphate and sodium cetyl sulphate; sodium dodecylbenzenesulphonate or sodium dioctyl sulphosuccinate; or fatty acids, in particular those derived from coconut oil, cationic surfactants, such as water-soluble quaternary ammonium salts of formula $N^+R'R''R'''R''''Y$, in which the R radicals are identical or different optionally hydroxylated hydrocarbon radicals and Y is an anion of a strong acid, such as halide, sulphate and sulphonate anions; cetyltrimethylammonium bromide is one of the cationic surfactants which can be used, amine salts of formula $N^+R'R''R'''$, in which the R radicals are identical or different optionally hydroxylated hydrocarbon radicals; octadecylamine hydrochloride is one of the cationic surfactants which can be used, non-ionic surfactants, such as optionally polyoxyethylenated esters of sorbitan, in particular Polysorbate 80, or polyoxyethylenated alkyl ethers; polyethylene glycol stearate, polyoxyethylenated derivatives of castor oil, polyglycerol esters, polyoxyethylenated fatty alcohols, polyoxyethylenated fatty acids or copolymers of ethylene oxide and of propylene oxide, amphoteric surfactants, such as substituted lauryl compounds of betaine, or preferably a mixture of at least two of the compounds listed above.

In a particular preferred embodiment, a crystallization inhibitor pair will be used. Such pairs include, for example, the combination of a film-forming agent of polymeric type and of a surface-active agent. These agents will be selected in particular from the compounds mentioned above as crystallization inhibitors.

Particularly preferred film-forming agents of polymeric type include:

the various grades of polyvinylpyrrolidone, polyvinyl alcohols, and copolymers of vinyl acetate and of vinylpyrrolidone.

Especially preferred surface-active agents, include those made of non-ionic surfactants, preferably polyoxyethylenated esters of sorbitan and in particular the various grades of polysorbate, for example Polysorbate 80.

The film-forming agent and the surface-active agent can in particular be incorporated in similar or identical amounts within the limit of the total amounts of crystallization inhibitor mentioned elsewhere.

The pair thus constituted secures, in a noteworthy way, the objectives of absence of crystallization on the coat and of maintenance of the cosmetic appearance of the fur, that is to say without a tendency towards sticking or towards a sticky appearance, despite the high concentration of active material.

Particularly preferred antioxidizing agents are those conventional in the art and include, for example, butylated hydroxyanisole, butylated hydroxytoluene, ascorbic acid, sodium metabisulphite, propyl gallate, sodium thiosulphate or a mixture of not more than two of them.

The formulation adjuvants discussed above are well known to the practitioner in this art and may be obtained commercially or through known techniques. These concentrated compositions are generally prepared by simple mixing of the constituents as defined above; advantageously, the starting point is to mix the active material in the main solvent and then the other ingredients or adjuvants are added.

The volume applied can be of the order of about 0.3 to about 1 ml, preferably of the order of about 0.5 ml, for cats and of the order of about 0.3 to about 3 ml for dogs, depending on the weight of the animal.

The formulations according to the invention are extremely effective for long durations of time in the treatment of parasites, such as mosquitoes in mammals and, in particular, of small mammals, such as dogs and cats. The inventive formulations also exhibit a degree of effectiveness against other parasitic insects, in particular, fleas, ticks, mites and flies.

Another method of formulating antiparasitical formulations in this invention is a bait formulation that comprises a at least one 1-N-arylpyrazole derivative and/or an IGR either alone or in combination with an antiparasitic, antihelmintic, or insecticidal agent placed in a commercially available bird station for preventing or interrupting the transmission of arthropod- or mosquito-borne diseases from an actual or putative amplifying or incipient host, such as an animal or bird (wild or domesticated), to a second actual or putative amplifying or incipient host, such as an animal, bird or human.

This invention further provides for an apparatus, which is a chamber comprising an opening, the interior of which includes an applicator that is attached to a reservoir by a conduit said conduit comprising an actuator to deliver a metered dose of a veterinary formulation comprising a 1-N-arylpyrazole, as well as a method for using the apparatus to prevent or interrupt the transmission for a mosquito-borne disease from a first actual or putative amplifying host, wherein said first host is a bird or animal, to a second actual or putative amplifying or incipient host in an environment where said first host resides by applying a metered dose of the veterinary formulation to the feathers, fur or skin of the bird or animal.

FIGS. 1 and 2 depict two non-limiting examples of the apparatus. To construct apparatuses of different sizes to accommodate a specific bird or animal would be well within the routine skill of the practitioner.

The apparatus (1) comprises a top, (2) a bottom (3), at least one wall (4), which connects the top (2) to the bottom (3), thereby creating an interior space (5), and at least one opening (6), which connects the environment (12) to the interior space (5) of the apparatus. The materials used for the top (2), bottom (3) and walls (4) would be well known to the practitioner and include, for example, wood, plastics, etc. FIG. 1 depicts a preferred embodiment of the apparatus that has four walls (4), one of which is removable (41) so one has the option of inserting bait or food (8). FIG. 2 depicts an alternative preferred embodiment, which has one wall (4), two openings (6), where the wall has a door (42) to insert the bait or food (not shown).

The interior space (61) of the opening (6) has an applicator (62) attached thereto. FIGS. 3(*a*) and 3(*b*) depict a detailed view of two preferred embodiments of the opening. The applicator (62) is attached to the reservoir (7), which contains the formulation (71) by a conduit (9), which conducts flow of the formulation (71) to the applicator (62). The applicator (62) comprises any material which will retain the formulation and transfer it to the bird or animal. Examples of suitable materials for an applicator would be a sponge or a moisture-sensitive membrane. Likewise, the reservoir and the conduit may be made of any material suitable for this purpose such as metal or plastic, and the size and shape depend on the particular dimensions of the apparatus. Such determinations for particular materials, size and shape are well within the review of the skilled practitioner.

Figure 3A:
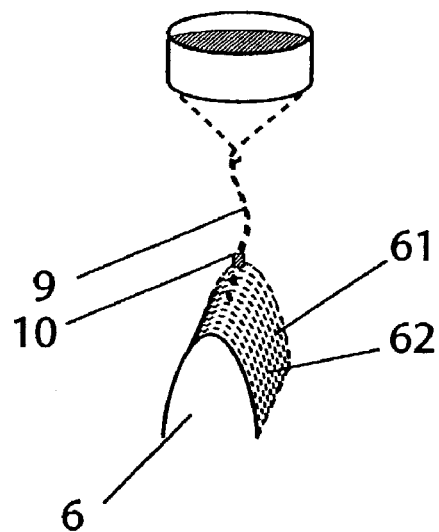
FIGS. 3a and 3b depict a detailed view of one embodiment of the opening in an apparatus made according to the present invention.
Figure 3B:
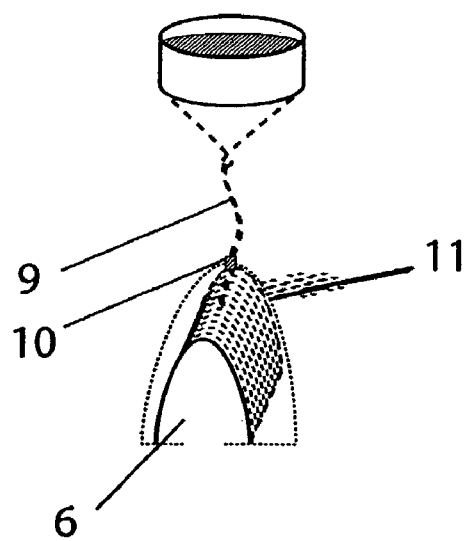

In FIGS. 3(a) and 3(b) the conduit (9) comprises an actuator (10) which administers the metered dose of the formulation when the bird or animal enters the apparatus. The activator may be, for example, a pressure sensitive device (not shown) or a light beam (11), which controls the release of the formulation to the applicator when the bird or animal enters or leaves the apparatus, thereby administering the metered dose of the formulation to the animal.

The opening (6) may be of any size or shape and is configured to permit the entry or egress of the bird or animal into the apparatus. The determination of the correct size would be well within the skill level of the practitioner and is dependent on the size of the bird or animal.

Other advantages and characteristics of the invention will become apparent on reading the following description, given by way of non-limiting examples.

EXAMPLE 1

Mosquito Mortality (Spray)

The ability of formulations to kill mosquitoes after feeding and thereby preventing or inhibiting the spread of a mosquito-borne disease was tested by comparing the mortality of mosquitoes who feed on dogs treated with a formulation comprising a 1-N-arylpyrazole derivative with dogs which were not treated.

Four beagles, two males and two females, were randomly assigned to one of two treatment groups. Group I was not treated and Group II was treated with a fipronil spray at a rate of 6 ml/kg on Day 0 and Day 30. Assessment of mosquito mortality was conducted by exposing the dogs of the two groups with non-infected mosquitoes on Days 3, 10, 17, 24, 31, 38, 45, 52 and 59. Mosquito mortality was determined by counting the number of dead mosquitoes 7 after exposure. The data is summarized in Table 2.

TABLE 1

Mosquito Mortality [engorged females]

| Days of Exposure* | | | | | | | | |
|---|---|---|---|---|---|---|---|---|
| 3 | 10 | 17 | 24 | 31 | 38 | 45 | 52 | 59 |
| 100% | 99% | 97% | 89% | 100% | 100% | 99% | 99% | 100% |

Dead Mosquitos 7 Days After Exposure

*Dogs are treated on day 0 and day 30.

The data demonstrates that there was an increase in the mortality of the mosquitoes that fed on dogs treated with a formulation comprising fipronil.

EXAMPLE 2

Mosquito Mortality (Spot-On Formulation)

The ability of a spot-on formulation comprising a 1-N-arylpyrazole derivative to kill mosquitoes in treated dogs was compared with untreated dogs.

Sixteen beagles were placed in two groups of eight dogs each. The dogs in group I were untreated and the dogs in group II were treated with topical fipronil, a spot-on formulation comprising 10% w/v of fipronil and 9% w/v of (s)-methoprene. The dogs were sedated and placed individually in mosquito proof containers. Approximately 100 mosquitoes, *A. aegypti* four to five days old were releases into the container. After approximately 30 minutes, all of the engorged and non-engorged mosquitoes were aspirated into a separate container using a vacuum pump and the number was recorded. Exposures occurred in days 1, 2, 7, 14, 21 and 28. Mosquitoes recovered from individual animals at each exposure were placed in separate containers (engorged and non-engorged) and kept in an insectary maintained at approximately 20° C. and 80% relative humidity for 2 days. At day 1 after exposure, all dead mosquitoes were removed and counted. At day 2, all dead mosquitoes were counted. The data is summarized below in Table 2.

TABLE 2

Mosquitoes Mortality after 48 hour post-exposure

| | | Fipronil Treated Dogs on Days Indicated After Treatment | | | | | |
|---|---|---|---|---|---|---|---|
| | | Day 1 | Day 2 | Day 7 | Day 14 | Day 21 | Day 28 |
| % Efficacy | 48 HR Count | 100.0 | 100.0 | 100.0 | 91.5 | 95.5 | 57.5 |

The results show that topical fipronil was effectively killing 95% of the mosquitoes at 3 weeks.

The above description is intended to be illustrative and not-limiting. Various changes or modifications in the embodiments described herein may occur to those skilled in the art. These can be made without departing from the scope or spirit of the invention.

The invention will now be further described by the following number paragraphs

1. A method for preventing or interrupting the transmission of mosquito-borne diseases from a first actual or putative amplifying or incipient host to a second actual or putative amplifying or incipient host, which comprises applying or administering a formulation comprising an effective amount of at least one 1-N-arylpyrazole to said first actual or putative amplifying host and/or actual or putative amplifying or incipient host.

2. The method according to paragraph 1, wherein the formulation comprises an effective amount of at least one 1-N-arylpyrazole is a compound of the formula

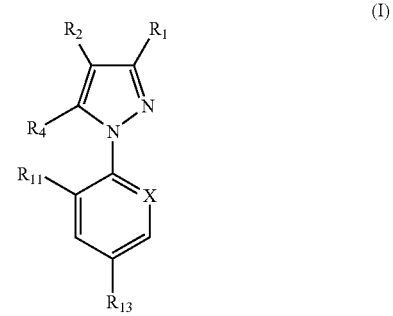

in which
R$_1$ is a halogen atom, CN or alkyl;
R$_2$ is S(O)$_n$R$_3$ or 4,5-dicyanoimidazol-2-yl or haloalkyl;
R$_3$ is alkyl, alkenyl, alkynyl, haloalkyl, haloalkenyl, or haloalkynyl;

$R_4$ represents a hydrogen or halogen atom or an $NR_5R_6$, $S(O)_mR_7$, $C(O)R_7$, $C(O)OR_7$, alkyl, haloalkyl, $OR_8$, or an —N=C($R_9$)($R_{10}$) group;

$R_5$ and $R_6$ independently represent a hydrogen atom or an alkyl, haloalkyl, C(O)alkyl, $S(O)_rCF_3$ or alkoxycarbonyl radical or $R_5$ and $R_6$ may form a ring of 3 to 7 members which is optionally interrupted by one or two divalent heteroatoms;

$R_7$ represents an alkyl or haloalkyl group;

$R_8$ represents an alkyl or haloalkyl group or a hydrogen atom;

$R_9$ represents an alkyl radical or a hydrogen atom;

$R_{10}$ represents an optionally substituted aryl or an optionally substituted heteroaryl group;

$R_{11}$ and $R_{12}$ represent, independently of one another, hydrogen, halogen CN or $NO_2$;

$R_{13}$ represents a halogen atom or a haloalkyl, haloalkoxy, $S(O)_qCF_3$ or $SF_5$ group;

m, n, q and r represent, independently of one another, an integer equal to 0, 1 or 2;

X represents a trivalent nitrogen atom or a C—$R_{12}$ radical, the three other valencies of the carbon atom forming part of the aromatic ring;

with the proviso that, when $R_1$ is methyl, then either $R_3$ is haloalkyl, $R_4$ is NH2, $R_{11}$ is Cl, $R_{13}$ is $CF_3$ and X is N or else $R_2$ is 4,5-dicyanoimidazol-2-yl, $R_4$ is Cl, $R_{11}$ is Cl, $R_{13}$ is $CF_3$ and X is C—Cl, optionally with a pharmaceutically acceptable carrier or excipient.

3. The method according to paragraph 2, wherein the formulation comprises an effective amount of a compound of formula (I) wherein:

$R_1$ is a halogen atom, CN or methyl;

$R_2$ is $S(O)_n R_3$ or 4,5-dicyanoimidazol-2-yl or haloalkyl;

$R_3$ is $C_1$-$C_6$-alkyl or $C_1$-$C_6$-haloalkyl;

$R_4$ represents a hydrogen or halogen atom; or a group $NR_5R_6$, $S(O)_mR_7$, $C(O)R_7$ or $C(O)OR_7$, alkyl, haloalkyl or $OR_8$ or a group —N=C($R_9$)($R_{10}$);

$R_5$ and $R_6$ independently represent a hydrogen atom or a $C_1$-$C_6$-alkyl, $C_1$-$C_6$-haloalkyl, C(O)$C_1$-$C_6$-alkyl, $S(O)_rCF3$, $C_1$-$C_6$-acyl or $C_1$-$C_6$-alkoxycarbonyl group; or $R_5$ and $R_6$ together may form a ring of 3- to 7-membered which additioanlly may contain one or more heteroatoms selected from the group consisting of oxygen or sulphur.

4. The method according to paragraph 1, wherein the formulation comprises an effective amount of at least 1-N-arylpyrazole is a compound of the formula

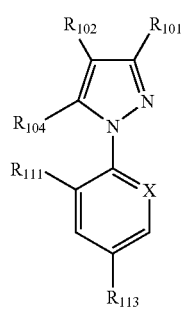

(II)

wherein:

$R_{101}$ is cyano, —C(O)alkyl, C(S)NH$_2$, alkyl, haloalkyl, C(=NOH)NH$_2$ or C(=NNH$_2$)NH$_2$;

$R_{102}$ is $S(O)_nR_{103}$, alkenyl, haloalkenyl, cycloalkyl, halocycloalkyl or alkynyl;

$R_{103}$ is alkyl or haloalkyl;

$R_{104}$ is —N=C($R_{105}$)—Z$R_{106}$, —N=C($R_{105}$)—N($R_{107}$)—$R_{108}$, or —N($R_{109}$)—($R_{105}$)=N$R_{106}$;

$R_{105}$ is hydrogen, alkyl, alkyl substituted by halogen, alkoxy, haloalkoxy or —S(O)$_mR_{105}$;

$R_{106}$ and $R_{107}$ each independently represent hydrogen, alkyl, alkenyl, alkynyl, alkyl substituted by one or more substituents selected from the group consists of halogen, alkoxy, haloalkoxy, amino, alkylamino, dialkylamino, cyano, —S(O)$_mR_{115}$, phenyl and pyridyl, said phenyl or pyridyl being optionally substituted with one or more substituents selected from the group consisting of halogen, nitro and alkyl, or $R_{106}$ and $R_{107}$ may form together with the nitrogen to which they are attached a 3- to 7-membered ring which may additionally contain one or more heteroatoms selected from the group consisting of oxygen, nitrogen or sulfur;

$R_{108}$ is alkoxy, haloalkoxy, amino, alkylamino, dialkylamino, $R_{114}$CO or —S(O)$_rR_{110}$;

$R_{109}$, $R_{110}$ and $R_{114}$ are alkyl or haloalkyl;

$R_{111}$ and $R_{112}$ are independently selected from the group consisting of halogen, hydrogen, CN and $NO_2$ $R_{113}$ is selected from the group consisting of halogen, haloalkyl, haloalkoxy, —S(O)$_qCF_3$, and —SF$_5$;

$R_{115}$ is alkyl or haloalkyl;

X is selected from nitrogen and C—$R_{112}$;

Z is O, $S(O)_{a'}$ or $NR_{107}$;

a', m', n' and q' are independently 0, 1, or 2; and t' is 0 or 2;

optionally with a pharmaceutically acceptable carrier or excipient.

5. The method according to paragraph 1, wherein the formulation comprises an effective amount of at least one 1-N-arylpyrazole of the formula:

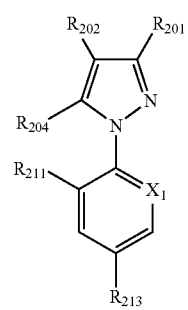

(III)

wherein:

$R_{201}$ is cyano, C(O)alkyl, C(S)N$_2$, alkyl, C(=NOH)NH$_2$ or C(=NNH$_2$)NH$_2$;

$R_{202}$ is $S(O)_nR_{203}$, alkenyl, haloalkenyl, cycloalkyl, halocycloalkyl or alkynyl;

$R_{203}$ is alkyl, alkenyl, alkynyl, haloalkenyl, or haloalkynyl;

$R_{204}$ is —N($R_{205}$)C(O)C$R_{206}R_{207}R_{208}$, —N($R_{205}$)C(O) aryl, or —N($R_{205}$)C(O)O$R_{207}$;

$R_{205}$ is alkyl, haloalkyl, cycloalkyl, halocycloalkyl, cycloalkylalkyl, halocycloalkylalkyl, alkoxyalkyl, haloalkoxyalkyl, alkenyl, haloalkenyl, alkynyl, haloalkynyl;

$R_{206}$ is hydrogen, halogen, alkoxy, haloalkoxy, alkoxyalkyl, haloalkoxyalkyl, formyloxy, alkylcarbonyloxy, haloalkylcarbonyloxy, alkylthio, haloalkylthio, alkylsulfinyl, haloalkylsulfinyl, alkylsulfonyl, haloalkylsulfonyl, alkylamino, dialkylamino, haloalkylamino, di(haloalkyl)amino, cycloalkyloxy, halocycloalkyloxy, alkoxyalkoxy, haloalkoxyalkoxy, alkoxyalkoxyalkoxy, aryloxy, or arylalkoxy;

$R_{207}$ and $R_{208}$ are independently hydrogen, alkyl, haloalkyl, cycloalkyl, or halocycloalkyl; or $R_{207}$ and $R_{208}$ may form together with the carbon to which they are attached a 3- to 7-membered ring which additionally may contain one or more heteroatoms selected from nitrogen, oxygen and sulfur;

$X_1$ is selected from nitrogen and $C-R_{212}$;

$R_{211}$ and $R_{212}$ are independently selected from the group consisting of halogen, hydrogen, CN and $NO_2$;

$R_{213}$ is selected from the group consisting of halogen, haloalkyl, haloalkoxy, $-S(O)_kCF_3$, and $-SF_5$; and h and k are independently selected from 0, 1, and 2;

optionally with a pharmaceutically acceptable carrier or excipient.

6. The method according to paragraph 5, wherein the formulation comprises an effective amount of at least 1-N-arylpyrazole of the formula (III), wherein $R_{201}$ is cyano;
$R_{203}$ is halomethyl;
$R_{204}$ is $N(R_{205})C(O)CR_{206}R_{207}R_{208}$;
$R_{211}$ and $R_{212}$ are independently halogen;
$X_1$ is $C-R_{212}$;
$R_{213}$ is haloalkyl, haloalkoxy or $-SF_5$; or
h is 0 or 1.

7. The method according to paragraph 1, wherein the formulation comprises an effective amount of at least one 1-N-arylpyrazole that is a compound selected from the group consisting of

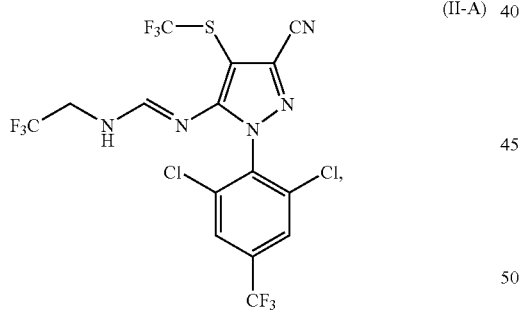

(II-A)

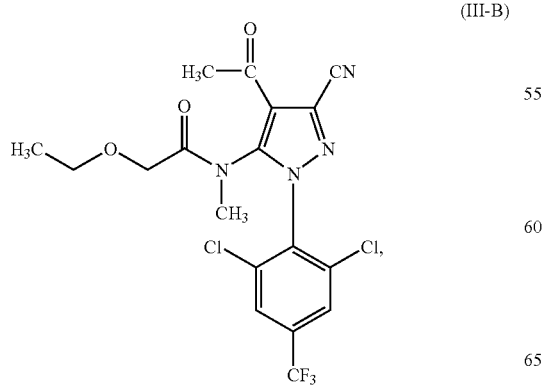

(III-B)

-continued

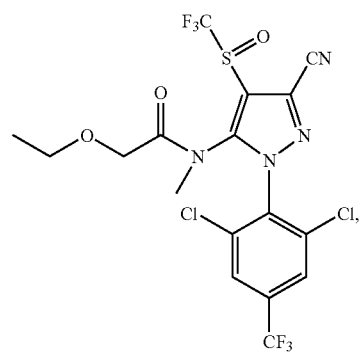

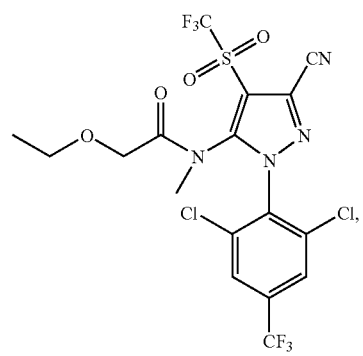

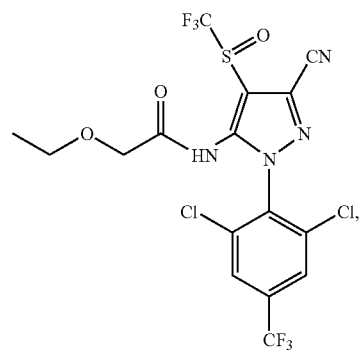

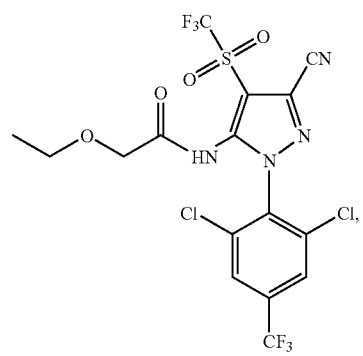

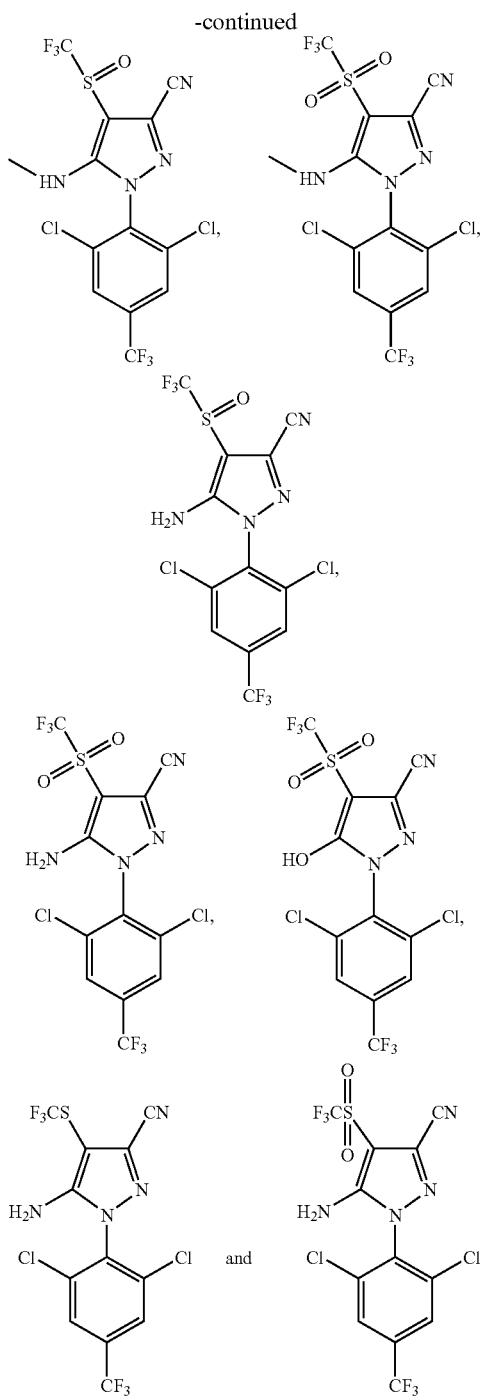

8. A method for preventing or interrupting the transmission of mosquito-borne diseases from an actual or putative amplifying or incipient host, to a second actual or putative amplifying or incipient host, by applying a spot-on formulation comprising:

(a) an effective amount of at least one 1-N-arylpyrazole derivative;
(b) a pharmaceutically acceptable liquid carrier vehicle;
(c) optionally, a crystallization inhibitor to said first actual or putative amplifying or incipient host and/or second actual or putative amplifying or incipient host.

9. The method according to paragraph 8 wherein the spot-on formulation comprises:
(a) an effective amount of at least one compound of the formula

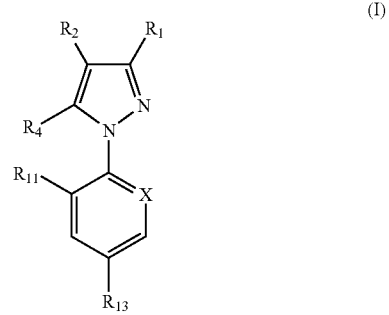

(I)

in which
$R_1$ is a halogen atom, CN or alkyl;
$R_2$ is $S(O)_nR_3$ or 4,5-dicyanoimidazol-2-yl or haloalkyl;
$R_3$ is alkyl, alkenyl, alkynyl, haloalkyl, haloalkenyl, or haloalkynyl;
$R_4$ represents a hydrogen or halogen atom or an $NR_5R_6$, $S(O)_mR_7$, $C(O)R_7$, $C(O)OR_7$, alkyl, haloalkyl, $OR_8$, or an $-N=C(R_9)(R_{10})$ group;
$R_5$ and $R_6$ independently represent a hydrogen atom or an alkyl, haloalkyl, C(O)alkyl, $S(O)_rCF_3$ or alkoxycarbonyl radical or $R_5$ and $R_6$ can together form a divalent alkylene radical which is optionally interrupted by one or two divalent heteroatoms;
$R_7$ represents an alkyl or haloalkyl group;
$R_8$ represents an alkyl or haloalkyl group or a hydrogen atom;
$R_9$ represents an alkyl group or a hydrogen atom;
$R_{10}$ represents an optionally substituted aryl or an optionally substituted heteroaryl group;
$R_{11}$ and $R_{12}$ represent, independently of one another, hydrogen, halogen CN or $NO_2$;
$R_{13}$ represents a halogen atom or a haloalkyl, haloalkoxy, $S(O)_qCF_3$ or $SF_5$ group;
m, n, q and r represent, independently of one another, an integer equal to 0, 1 or 2;
X represents a trivalent nitrogen atom or a C—$R_{12}$ radical, the three other valencies of the carbon atom forming part of the aromatic ring;
with the proviso that, when RI is methyl, then either $R_3$ is haloalkyl, $R_4$ is $NH_2$, $R_{11}$ is Cl, $R_{13}$ is $CF_3$ and X is N or else $R_2$ is 4,5-dicyanoimidazol-2-yl, $R_4$ is Cl, $R_{11}$ is Cl, $R_{13}$ is $CF_3$ and X is C—Cl;
(b) a pharmaceutically or veterinary acceptable liquid carrier vehicle; and
(c) optionally, a crystallization inhibitor.

10. The method according to paragraph 8 wherein
the liquid carrier vehicle comprises a solvent and a cosolvent wherein the solvent is selected from the group consisting of acetone, acetonitrile, benzyl alcohol, butyl diglycol, dimethylacetamide, dimethylformamide, dipropylene glycol n-butyl ether, ethanol, isopropanol, methanol, ethylene glycol monoethyl ether, ethylene glycol monomethyl ether, monomethylacetamide, dipropylene glycol monomethyl ether, liquid polyoxyethylene glycols, propylene glycol, 2-pyrrolidone, diethylene glycol monoethyl ether, ethylene glycol, diethyl phthalate fatty acid esters, and a mixture of at least two of these solvents and the cosolvent is selected from the group consisting of absolute ethanol, isopropanol or methanol.

the crystallization inhibitor selected from the group consisting of an anionic surfactant, a cationic surfactant, a non-ionic surfactant, an amine salt, an amphoteric surfactant or polyvinylpyrrolidone, polyvinyl alcohols, copolymers of vinyl acetate and vinylpyrrolidone, polyethylene glycols, benzyl alcohol, mannitol, glycerol, sorbitol, polyoxyethylenated sorbitan esters, lecithin, sodium carboxymethylcellulose, and acrylic derivatives, and a mixture of these crystallization inhibitors.

11. The method according to paragraph 9, wherein the formulation comprises an effective amount of a compound of formula (I) wherein
$R_1$ is a halogen atom, CN or methyl;
$R_2$ is $S(O)_n R_3$ or 4,5-dicyanoimidazol-2-yl or haloalkyl;
$R_3$ is $C_1$-$C_6$-alkyl or $C_1$-$C_6$-haloalkyl;
$R_4$ represents a hydrogen or halogen atom; or a group $NR_5R_6$, $S(O)_m R_7$, $C(O)R_7$ or $C(O)OR_7$, alkyl, haloalkyl or $OR_8$ or a group —N=C($R_9$)($R_{10}$);
$R_5$ and $R_6$ independently represent a hydrogen atom or a $C_1$-$C_6$-alkyl, $C_1$-$C_6$-haloalkyl, $C(O)C_1$-$C_6$-alkyl, $S(O)_r CF_3$, $C_1$-$C_6$-acyl or $C_1$-$C_6$-alkoxycarbonyl group; or $R_5$ and $R_6$ may together form a divalent alkylene group which may be interrupted by one or two divalent hetero atoms selected from the group consisting of oxygen or sulphur.

12. The method according to paragraph 10, wherein the formulation comprises an effective amount of at least one 1-N-arylpyrazole is a compound of the formula

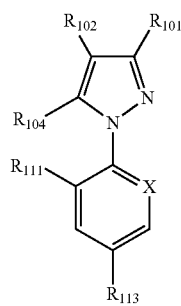

(II)

wherein:
$R_{101}$ is cyano, —C(O)alkyl, C(S)NH$_2$, alkyl, haloalkyl, C(=NOH)NH$_2$ or C(=NNH$_2$)NH$_2$;
$R_{102}$ is $S(O)_n R_{103}$, alkenyl, haloalkenyl, cycloalkyl, halocycloalkyl or alkynyl;
$R_{103}$ is alkyl, alkenyl, alkynyl, haloalkyl, haloalkenyl, or haloalkynyl;
$R_{104}$ is —N=C($R_{105}$)—Z—$R_{106}$, —N=C($R_{105}$)—N($R_{107}$)—$R_{108}$; or —N($R_{109}$)—C($R_{105}$)=N$R_{106}$;
$R_{105}$ is hydrogen, alkyl, or alkyl substituted by halogen, alkoxy, haloalkoxy, or —S(O)m'$R_{105}$;
$R_{106}$ and $R_{107}$ each independently represent hydrogen, alkyl, alkenyl or alkynyl, alkyl substituted by one or more substituents selected from the group consisting of halogen, alkoxy, haloalkoxy, amino, alkylamino, dialkylamino, cyano —S(O)$_m R_{115}$, phenyl and pyridyl, said phenyl or pyridy being is optionally substituted with one or more substituents selected from the group consisting of halogen, nitro and alkyl; or $R_{106}$ and $R_{107}$ may form together with the nitrogen to which they are attached a 3- to 7-membered ring which may additionally contain one or more heteroatoms selected from the group consisting of oxygen, nitrogen or sulfur;
$R_{108}$ is alkoxy, haloalkoxy, amino, alkylamino, dialkylamino, $R_{114}$CO— or —S(O)$_t R_{110}$;
$R_{109}$, $R_{110}$ and $R_{114}$ are alkyl or haloalkyl;
$R_{111}$ and $R_{112}$ are independently selected from the group consisting of halogen, hydrogen, CN and NO$_2$;
$R_{113}$ is selected from the group consisting of halogen, haloalkyl, haloalkoxy, —S(O)$_q$CF$_3$, and —SF$_5$;
$R_{115}$ is alkyl or haloalkyl;
X is nitrogen or C—$R_{112}$;
Z is O, S(O)$_{a'}$ or NR$_{107}$;
a', m', n' and q' are independently 0, 1, or 2; and
t' is 0 or 2;
optionally with a pharmaceutically acceptable carrier or excipient.

13. The method according to paragraph 10, wherein the formulation comprises an effective amount of at least one 1-N-arylpyrazole of the formula:

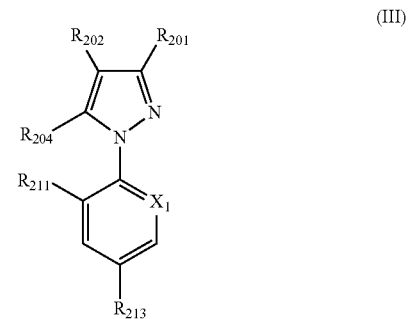

(III)

wherein:
$R_{201}$ is cyano, C(O)alkyl, C(S)NH$_2$, alkyl, C(=NOH)NH$_2$ or C(=NNH$_2$)NH$_2$;
$R_{202}$ is S(O)$_n R_{203}$, alkenyl, haloalkenyl, cycloalkyl, halocycloalkyl or alkynyl;
$R_{203}$ is alkyl, alkenyl, alkynyl, haloalkyl, haloalkenyl, or haloalkynyl;
$R_{204}$ is —N($R_{205}$)C(O)C$R_{206}R_{207}R_{208}$, —N($R_{205}$)C(O) aryl, or —N($R_{205}$)C(O)OR$_{207}$;
$R_{205}$ is alkyl, haloalkyl, cycloalkyl, halocycloalkyl, cycloalkylalkyl, halocycloalkylalkyl, alkoxyalkyl, haloalkoxyalkyl, alkenyl, haloalkenyl, alkynyl, haloalkynyl;
$R_{206}$ is hydrogen, halogen, alkoxy, haloalkoxy, alkoxyalkyl, haloalkoxyalkyl, formyloxy, alkylcarbonyloxy, haloalkylcarbonyloxy, alkylthio, haloalkylthio, alkylsulfinyl, haloalkylsulfinyl, alkylsulfonyl, haloalkylsulfonyl, alkylamino, dialkylamino, haloalkylamino, di(haloalkyl)amino, cycloalkyloxy, halocycloalkyloxy, alkoxyalkoxy, haloalkoxyalkoxy, alkoxyalkoxyalkoxy, aryloxy, or arylalkoxy;
$R_{207}$ and $R_{208}$ are independently hydrogen, alkyl, haloalkyl, cycloalkyl, or halocycloalkyl; or $R_{207}$ and $R_{208}$ may form together with the carbon to which they are attached a 3- to 7-membered ring which additionally may contain one or more heteroatoms selected from the group consisting of nitrogen, oxygen and sulfur;

$X_1$ is nitrogen or C—$R_{212}$;

$R_{211}$ and $R_{212}$ are independently selected from the group consisting of halogen, hydrogen, CN and $NO_2$;

$R_{213}$ is selected from the group consisting of halogen, haloalkyl, haloalkoxy, —S(O)$_k$CF$_3$, and —SF$_5$;

and h and k are independently selected from 0, 1, and 2;

optionally with a pharmaceutically acceptable carrier or excipient.

14. The method according to paragraph 13, wherein the formulation comprises an effective amount of at least one 1-N-arylpyrazole of the formula (III), wherein $R_{201}$ is cyano;

$R_{203}$ is halomethyl;

$R_{204}$ is N($R_{205}$)C(O)C$R_{206}R_{207}R_{208}$;

$R_{211}$ and $R_{212}$ are independently halogen;

$X_1$ is C—$R_{212}$;

$R_{213}$ is haloalkyl, haloalkoxy or —SF$_5$; or h is 0 or 1.

15. The method according to paragraph 10, wherein the formulation comprises an effective amount of at least one 1-N-arylpyrazole selected from the group consisting of

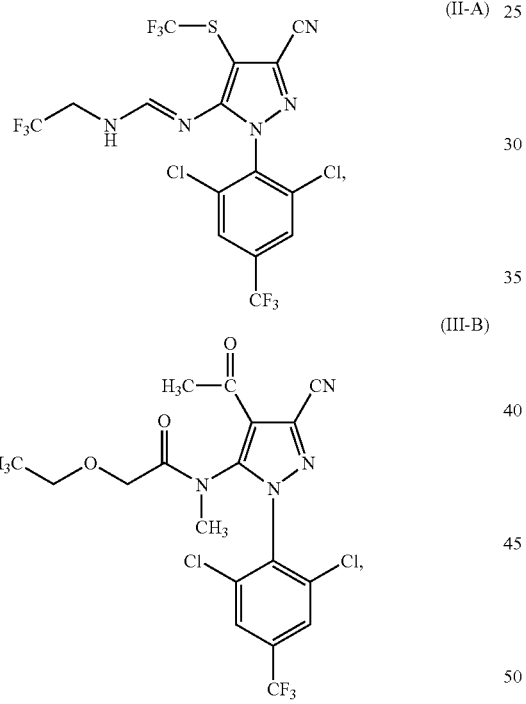

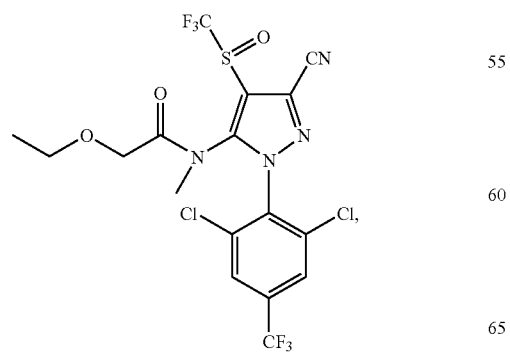

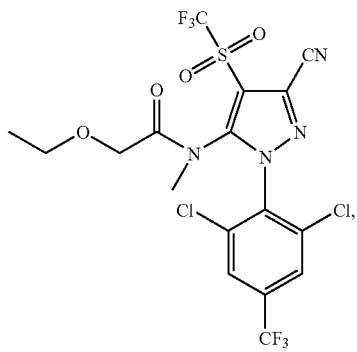

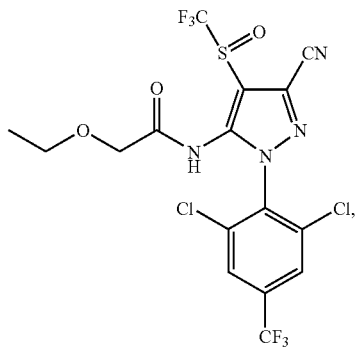

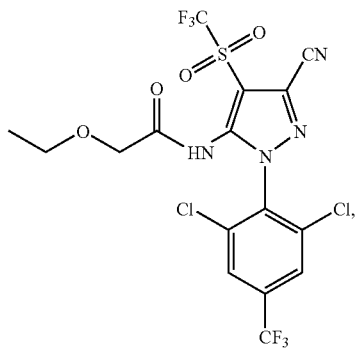

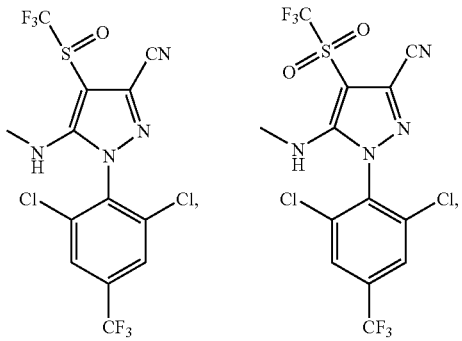

-continued

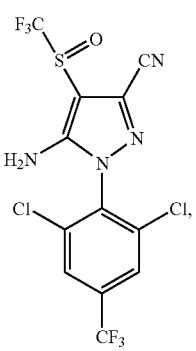

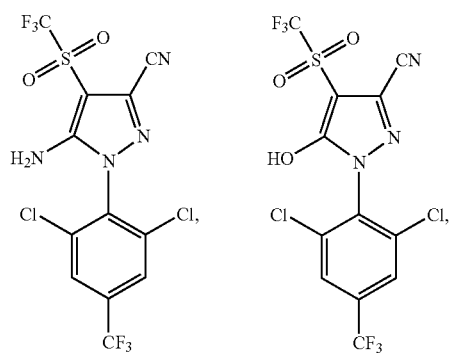

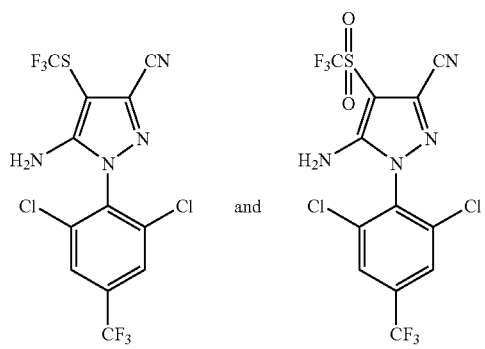

16. The method according to paragraph 15, wherein the formulation further comprises an insect growth regulator.

17. The method according to paragraph 1, wherein the formulation is a pour-on formulation.

18. The method according to paragraph 17, wherein the pour-on formulation comprises:
(a) an effective amount of at least one 1-N-arylpyrazole derivative;
(b) a pharmaceutically or veterinary acceptable liquid carrier vehicle which comprise a solvent and a cosolvent wherein the solvent is selected from the group consisting of acetone, acetonitrile, benzyl alcohol, butyl diglycol, dimethylacetamide, dimethylformamide, dipropylene glycol n-butyl ether, ethanol, isopropanol, methanol, ethylene glycol monoethyl ether, ethylene glycol monomethyl ether, monomethylacetamide, dipropylene glycol monomethyl ether, liquid polyoxyethylene glycols, propylene glycol, 2-pyrrolidone, diethylene glycol monoethyl ether, ethylene glycol, diethyl phthalate, fatty acid esters and a mixture of at least two of these solvents and the cosolvent is selected from the group consisting of absolute ethanol, isopropanol and methanol;
(c) a crystallization inhibitor selected from the group consisting of an anionic surfactant, a cationic surfactant, a nonionic surfactant, anamine salts, amphoteric surfactant, polyvinylpyrrolidone, polyvinyl alcohols, copolymers of vinyl acetate and vinylpyrrolidone, polyethylene glycols, benzyl alcohol, mannitol, glycerol, sorbitol, polyoxyethylenated sorbitan esters; lecithin, sodium carboxymethylcellulose, acrylic derivatives and a mixture of these crystallization inhibitors;
(d) optionally, an antioxidant.

19. The method according to paragraph 18 wherein the 1-N-arylpyrazole is

1-[2,6-Cl$_2$-4-CF$_3$ phenyl]-3-CN-4-[SO—CF$_3$]-5-NH$_2$ pyrazole; or

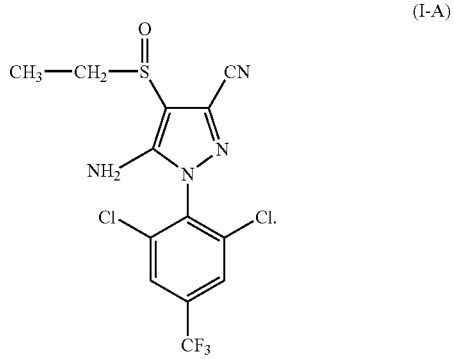

(I-A)

20. The method according to paragraph 18 wherein the 1-N-arylpyrazole is

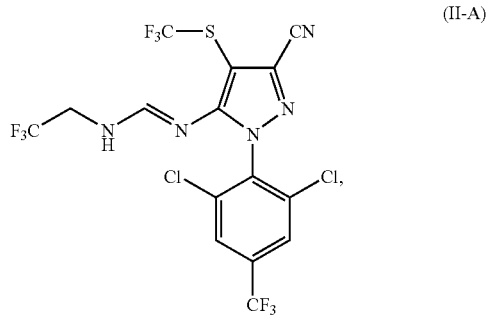

(II-A)

-continued
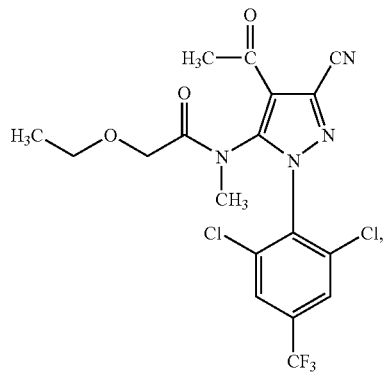
(III-B)
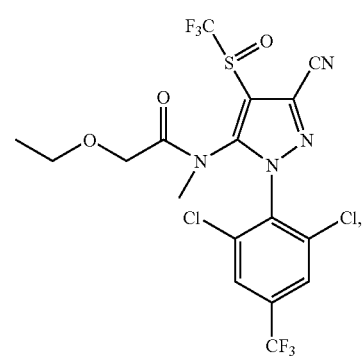
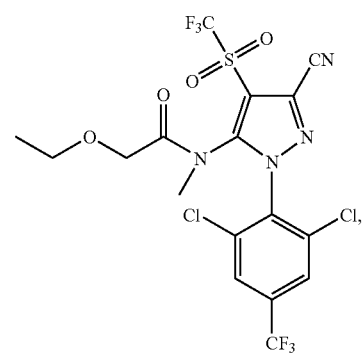
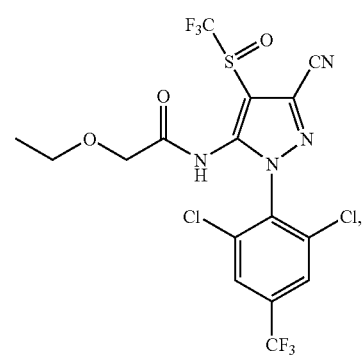
-continued
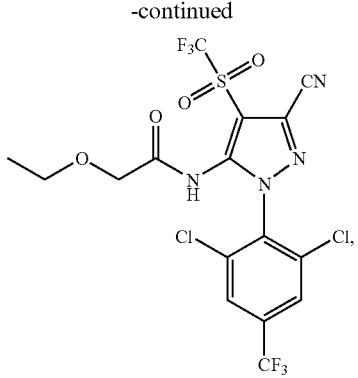
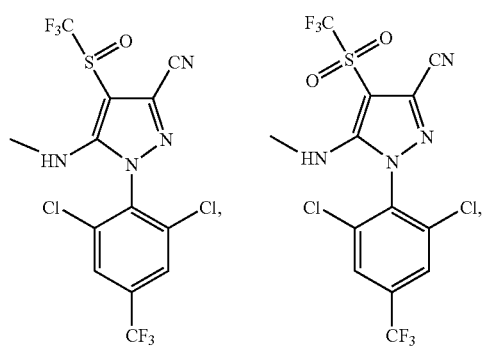
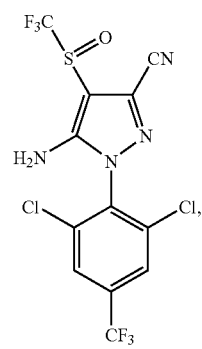
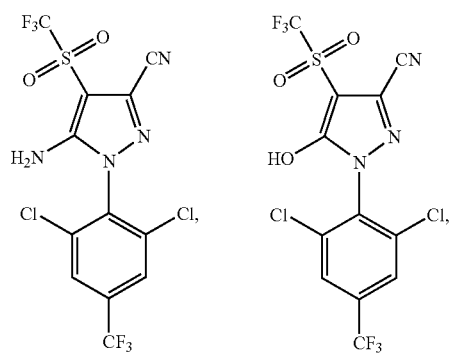

-continued

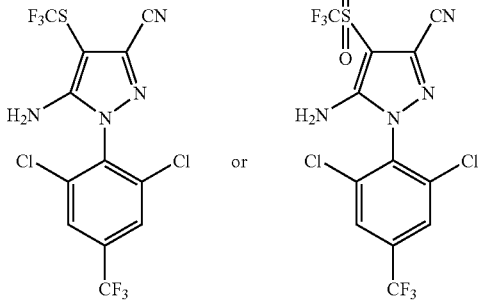

What is claimed is:

1. A method for interrupting the transmission of mosquito-borne diseases from a first actual or putative amplifying or incipient host, which is a bird, to a second actual or putative amplifying or incipient host, which is a horse, which comprises applying or administering a formulation comprising at least one 1-N-arylpyrazole derivative to said first actual or putative amplifying or incipient host in an amount capable of killing mosquitoes after feeding on the first actual or putative amplifying or incipient host and thereby interrupting the transmission of mosquito-borne diseases from the first actual or putative amplifying or incipient host to the second actual or putative amplifying or incipient host, wherein the at least 1-N-arylpyrazole derivative has the formula

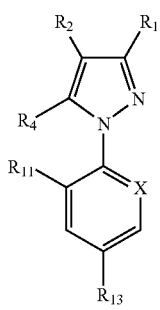
(I)

in which
R$_1$ is CN;
R$_2$ is S(O)$_n$R$_3$;
R$_3$ is haloalkyl;
R$_4$ is NH$_2$;
R$_{11}$ and R$_{12}$ represent, independently of one another, a halogen atom;
R$_{13}$ is a haloalkyl;
n is an integer equal to 0, 1 or 2;
X is a C—R$_{12}$ radical; and
the formulation is suitable for applying or administering the 1-N-arylpyrazole to a bird.

2. The method of claim 1, wherein the formulation is a spot-on formulation.

3. The method according to claim 2 wherein the formulation comprises
a solvent and a cosolvent wherein the solvent is selected from the group consisting of acetone, acetonitrile, benzyl alcohol, butyl diglycol, dimethylacetamide, dimethylformamide, dipropylene glycol n-butyl ether, ethanol, isopropanol, methanol, ethylene glycol monoethyl ether, ethylene glycol monomethyl ether, monomethylacetamide, dipropylene glycol monomethyl ether, liquid polyoxyethylene glycols, propylene glycol, 2-pyrrolidone, diethylene glycol monoethyl ether, ethylene glycol, diethyl phthalate fatty acid esters, and a mixture of at least two of these solvents and the cosolvent is selected from the group consisting of ethanol, isopropanol or methanol; and optionally
a crystallization inhibitor selected from the group consisting of an anionic surfactant, a cationic surfactant, a non-ionic surfactant, an amine salt, an amphoteric surfactant or polyvinylpyrrolidone, a polyvinyl alcohol, a copolymer of vinyl acetate and vinylpyrrolidone, a polyethylene glycol, benzyl alcohol, mannitol, glycerol, sorbitol, a polyoxyethylenated sorbitan ester, lecithin, sodium carboxymethylcellulose, and an acrylic derivative, and a mixture of these crystallization inhibitors.

4. The method of claim 3 wherein the formulation includes the crystallization inhibitor.

5. The method according to claim 3, wherein the 1-N-arylpyrazole derivative is 5-amino-3-cyano-1-(2,6-dichloro-4-trifluoromethylphenyl)-4-trifluoromethylsulfinylpyrazole (fipronil).

6. The method according to claim 3, wherein the formulation further comprises an antioxidant.

7. The method according to claim 6, wherein the antioxidant is selected from the group consisting of butylated hydroxyanisole, butylated hydroxytoluene, ascorbic acid, sodium metabisulphite, propyl gallate and sodium thiosuphate.

8. The method of claim 3 wherein in the formulation, water is present in a proportion of from 0 to about 30% V/V.

9. The method of claim 4 wherein in the formulation, the crystallization inhibitor is present in an amount from about 1 to about 20% W/V.

10. The method of claim 3 or 4 wherein in the formulation,
the anionic surfactant is an alkaline stearate, sodium abietate; an alkyl sulphate; sodium dodecylbenzenesulphonate, sodium dioctylsulphosuccinate; and a fatty acid;
the cationic surfactant is water-soluble quaternary ammonium salts of formula N$^+$R'R''R'''R''''Y in which the radicals R independently are hydrocarbon radicals, optionally hydroxylated, and Y is an anion of a strong acid; cetyltrimethylammonium bromide or octadecylamine hydrochloride;
the amine salt is an amine salt of N$^+$R'R''R''' in which the radicals R independently are optionally hydroxylated hydrocarbon radicals;
the non-ionic surfactant is optionally a polyoxyethylenated sorbitan ester, a polyoxyethylenated alkyl ether; polyethylene glycol stearate, a polyoxyethylenated derivative of castor oil, a polyglycerol ester, a polyoxyethylenated fatty alcohol, a polyoxyethylenated fatty acid, a copolymer of ethylene oxide and propylene oxide; and
the amphoteric surfactant is lauryl-substituted betaine compounds.

11. The method of claim 3 or 4 wherein in the formulation, the crystallization inhibitor is a crystallization inhibitor system comprising a polymeric film-forming agent and a surfactant.

12. The method of claim 11 wherein in the spot-on formulation the polymeric film-forming agent is polyvinylpyrrolidone, polyvinyl alcohols, or a copolymer of vinyl acetate and polyvinylpyrrolidone and the surfactant is a non-ionic surfactant.

13. The method of claim 4 wherein the crystallization inhibitor system is a mixture of polyvinylpyrrolidone and polyoxethylene (20) sorbitan mono-oleate.

14. The method according to claim 6, wherein the liquid carrier vehicle comprises diethylene glycol monomethylether and ethanol, the crystallization inhibitor is a mixture of polyvinylpyrrolidone and Tween 80, and the antioxidant is butylhydroxytoluene.

15. The method according to claim 5, wherein the formulation comprises diethylene glycol monomethylether, ethanol, and polyvinylpyrrolidone.

16. The method of claim 3 or 4 wherein:
the crystallization inhibitor selected from the group consisting of polyvinylpyrrolidone, copolymers of vinyl acetate and vinylpyrrolidone, polyoxyethylenated sorbitan esters and mixtures thereof;
the organic solvent comprises acetone, ethyl acetate, methanol, ethanol, isopropanol, dimethylformamide, dichloromethane or diethyl glycol monoethyl ether; said solvent optionally supplemented by $C_8$-$C_{10}$ caprylic/capric triglyceride, oleic acid or propylene glycol; and
the organic cosolvent is selected from the group consisting of ethanol, isopropanol, and methanol.

17. The method according to claim 1, 2, 3, 4, 5, 14 or, 15, wherein the mosquito-borne disease is caused by a virus.

18. The method according to claim 17, wherein the virus is the West Nile virus, the virus that causes Eastern Equine Encephalitis (EEE), Western Equine Encephalitis (WEE), or the virus that causes St. Louis Encephalitis (SLE).

19. The method according to claim 1, 2, 3, 4, 5, 14 or, 15, wherein the formulation further comprises an insect growth regulator having juvenile hormones activity.

20. The method according to claim 19, wherein the insect growth regulator is selected from the group consisting of azadirachtin, diofenolan, fenoxycarb, hydroprene, kinoprene, methoprene, pyriproxyfen, tetrahydroazadirachtin, and 4-chloro-2-(2-chloro-2-methyl-propyl)-5-(6-iodo-3-pyridylmethoxy)pyridizine-3(2H)-one.

21. The method according to claim 20, wherein the 1-N-arylpyrazole is fipronil and the insect growth regulator is (s)-methoprene.

22. The method according to claim 19, wherein the formulation comprises from about 2 to about 10 mg/kg of body weight of 1-N-arylpyrazole and from about 2 to about 20 mg/kg of body weight of insect growth regulator.

23. The method according to claim 19 wherein the mosquito borne disease is caused by a virus.

24. The method according to claim 23, wherein the virus is the West Nile virus, the virus that causes Eastern Equine Encephalitis (EEE), Western Equine Encephalitis (WEE), or the virus that causes St. Louis Encephalitis (SLE).

25. The method according to claim 10, wherein the alkaline stearate is a sodium, potassium or ammonium stearate; a calcium stearate or a triethanolamine stearate.

26. The method according to claim 10, wherein the alkyl sulphate is a sodium lauryl sulphate, a sodium cetyl sulphate, a sodium dodecylbenzenesulphonate or a sodium dioctyl sulphosuccinate.

27. The method according to claim 10, wherein the non-ionic surfactant is polysorbate 80 or polyethylene glycol stearate.

28. The method according to claim 12 wherein the non-ionic surfactant is a polyoxyethylated sorbitan ester or a polysorbate.

* * * * *

UNITED STATES PATENT AND TRADEMARK OFFICE
CERTIFICATE OF CORRECTION

PATENT NO.        : 7,262,214 B2                                  Page 1 of 1
APPLICATION NO.   : 10/374627
DATED             : August 28, 2007
INVENTOR(S)       : Mark Soll and Albert Boeckh It is certified that error appears in the above-identified patent and that said Letters Patent is hereby corrected as shown below:

IN THE CLAIMS:

Column 45, claim 10 should read:

-- The method of claim 3 or 4 wherein in the formulation,

- the anionic surfactant is an alkaline stearate, sodium abietate; an alkyl sulphate; sodium dodecylbenzenesulphonate, sodium dioctylsulphosuccinate; and a fatty acid;
- the cationic surfactant is water-soluble ~~quatemary~~ quaternary ammonium salts of formula $N^+R'R''R'$ "R" $Y^-$ in which the radicals R independently are hydrocarbon radicals, optionally hydroxylated, and $Y^-$ is an anion of a strong acid; cetyltrimethylammonium bromide or octadecylamine hydrochloride.
- the amine salt is an amine salt of $N^+R'R''R'$ " in which the radicals R independently are optionally hydroxylated hydrocarbon radicals;
- the non-ionic surfactant is optionally a polyoxyethylenated sorbitan ester, a polyoxyethylenated alkyl ether; polyethylene glycol stearate, a polyoxyethylenated derivative of castor oil, a polyglycerol ester, a polyoxyethylenated fatty alcohol, a polyoxyethylenated fatty acid, a copolymer of ethylene oxide and propylene oxide; and
- the amphoteric surfactant is lauryl-substituted betaine compounds. --

Signed and Sealed this

Fifteenth Day of January, 2008

JON W. DUDAS
*Director of the United States Patent and Trademark Office*